(12) United States Patent
Ogawa et al.

(10) Patent No.: US 9,227,018 B2
(45) Date of Patent: Jan. 5, 2016

(54) PRE-USE MIXING PRE-FILLED SYRINGE

(71) Applicants: TAISEI KAKO CO., LTD., Osaka (JP); SUZUKEN CO., LTD., Aichi (JP)

(72) Inventors: Yukihiro Ogawa, Osaka (JP); Ichiro Suzuki, Aichi (JP)

(73) Assignees: Taisei Kako Co. Ltd., Osaka (JP); Suzuken Co., Ltd., Aichi (JP)

( * ) Notice: Subject to any disclaimer, the term of this patent is extended or adjusted under 35 U.S.C. 154(b) by 0 days.

(21) Appl. No.: 14/384,793

(22) PCT Filed: Apr. 14, 2013

(86) PCT No.: PCT/JP2013/057165
§ 371 (c)(1),
(2) Date: Sep. 12, 2014

(87) PCT Pub. No.: WO2013/137383
PCT Pub. Date: Sep. 19, 2013

(65) Prior Publication Data
US 2015/0100018 A1    Apr. 9, 2015

(30) Foreign Application Priority Data
Mar. 16, 2012  (JP) .................... 2012-059507

(51) Int. Cl.
*A61M 5/31* (2006.01)
*A61M 5/28* (2006.01)
*A61M 5/32* (2006.01)
*A61M 5/315* (2006.01)

(52) U.S. Cl.
CPC .............. *A61M 5/284* (2013.01); *A61M 5/28* (2013.01); *A61M 5/283* (2013.01); *A61M 5/288* (2013.01); *A61M 5/326* (2013.01); *A61M 5/31596* (2013.01)

(58) Field of Classification Search
CPC ...... A61M 5/283; A61M 5/284; A61M 5/288; A61M 5/31596; A61M 5/3294; A61M 5/2448; A61M 2005/247; A61M 2005/2474
See application file for complete search history.

(56) References Cited

U.S. PATENT DOCUMENTS

| | | | |
|---|---|---|---|
| 5,102,388 A * | 4/1992 | Richmond | ............ 604/88 |
| 6,349,850 B1 * | 2/2002 | Cheikh | ............ 222/1 |

(Continued)

FOREIGN PATENT DOCUMENTS

| | | |
|---|---|---|
| BE | 1018797 A3 | 9/2011 |
| EP | 0709106 A2 | 5/1996 |

(Continued)

OTHER PUBLICATIONS
European Search Report dated Jul. 15, 2015.
(Continued)

*Primary Examiner* — Nicholas Lucchesi
*Assistant Examiner* — Justin L Zamory
(74) *Attorney, Agent, or Firm* — Wood, Phillips, Katz, Clark & Mortimer

(57) ABSTRACT

A prefilled syringe of a before-use mixing type not requiring a bypass portion defined by a recessed inner surface portion of an outer cylinder, including first and second gaskets (4,5) fitted in the outer cylinder (2), and non-rotatively and complementarily shaped engagement portions (12, 13) respectively at a front end of the first gasket (4) and a rear end of the second gasket (5) to reduce the period for transferring a liquid between two chambers separated by the gaskets. During storage, the engagement portions abut each other to be kept out of engagement with each other, whereby a drug containing space is defined between the gaskets. When a liquid is transferred from a space defined on a rear side of the first gasket (4) to the drug containing space, the internal pressure of the drug containing space is prevented from being excessively increased.

13 Claims, 30 Drawing Sheets

(56) References Cited

U.S. PATENT DOCUMENTS

2003/0199816 A1    10/2003    Ramming
2012/0016296 A1*    1/2012    Charles ............... A61M 5/2066
                                                            604/87

FOREIGN PATENT DOCUMENTS

| GB | 2362811 A | 2/2010 |
|---|---|---|
| JP | 2002177388 A | 6/2002 |
| JP | 200393509 A | 4/2003 |
| JP | 200497583 A | 4/2004 |
| WO | 01/30424 A1 | 5/2001 |

OTHER PUBLICATIONS

International Search Report dated Jun. 18, 2013.

* cited by examiner

PRE-USE MIXING PRE-FILLED SYRINGE

CROSS-REFERENCE TO RELATED APPLICATIONS

This is a National Stage Application based on PCT/JP2013/057165, filed Mar. 14, 2013 which is based on Japanese Patent Application No. JP 2012-059,507, filed Mar. 16, 2012.

TECHNICAL FIELD

The present invention relates to a prefilled syringe of before-use mixing type.

BACKGROUND ART

Prefilled syringes of a before-use dissolving type disclosed in the following PLT1 to PLT4 are conventionally known.

CITATION LIST

Patent Literature

PLT1: JP-2001-104482-A
PLT2: JP-HEI8 (1996)-112333-A
PLT3: JP-2003-190284-A
PLT4: JP-2011-67265-A

In the prefilled syringes disclosed in PLT2 to PLT4, a bypass passage is defined by a recessed inner surface portion of an outer cylinder, and a center gasket is fitted in the outer cylinder on a rear side of the bypass passage. A first liquid is sealed in a space defined on a rear side of the center gasket, while a freeze-dried drug or a second liquid is sealed in a space defined on a front side of the center gasket. When the center gasket is pushed forward for use, the bypass passage is opened, so that the spaces on the front and rear sides of the center gasket communicate with each other. Thus, the first liquid flows into the front space from the rear space, whereby the freeze-dried drug or the second liquid is dissolved in or mixed with the first liquid.

The current trend of the prefilled syringe of the before-use dissolving type is toward those having the bypass passage. However, it is not easy to form a recess in an inner surface of a cylindrical syringe by molding, so that a special mechanism should be provided in a mold. Further, additional time is required for a preparatory operation to be performed for this special mechanism before the molding, and for demolding and cleaning steps to be performed after the molding. Problematically, this reduces the mass productivity, and increases the production costs.

The prefilled syringe of the before-use mixing type disclosed in PLT1 is known to solve the aforementioned problem. According to PLT1, the outer cylinder of the syringe has a common structure such that no bypass passage is provided in the inner surface thereof. The syringe includes a first gasket, a second gasket and a third gasket fitted in the outer cylinder in axially spaced relation. A powdery drug is contained in a first containing portion defined in the outer cylinder on a front side of the foremost first gasket. A cavity is defined between the first gasket and the middle second gasket. A liquid for dissolving the drug is contained in a second containing portion defined in the outer cylinder between the second gasket and the rearmost third gasket. The first gasket is provided with a hollow needle which, when the second and third gaskets are moved forward, penetrates through the second gasket to cause the first containing portion and the second containing portion to communicate with each other.

When the third gasket is gradually pushed forward, therefore, air is moved into the first containing portion from the cavity defined between the first and second gaskets, and the hollow needle fixed to the first gasket penetrates through the second gasket to establish the communication between the first containing portion and the second containing portion as described in a paragraph [0016] in PTL1. When the third gasket is pushed in the outer cylinder, the liquid is gradually moved from the second containing portion to the first containing portion. With the third gasket in abutment against the second gasket, all the liquid finally flows into the first containing portion. The drug is dissolved in the liquid thus flowing into the first containing portion. A cap is removed from an injection needle, and air is expelled from the first containing portion. Thus, preparation for administration of the drug solution to a patient is completed.

SUMMARY OF INVENTION

Technical Problem

The components of the syringe disclosed in PLT1 each have a simplified structure. Therefore, the syringe can be easily produced at higher mass productivity, but disadvantageously requires a longer period of time for the preparation for the administration to the patient. That is, when the third gasket is pushed after the communication between the first containing portion and the second containing portion is established, a pushing force also acts on the first gasket. Therefore, the internal pressure of the first containing portion is increased to substantially the same level as the internal pressure of the second containing portion, so that the liquid gradually flows into the first containing portion from the second containing portion with time by a slight pressure difference between the first and second containing portions.

It is therefore an object of the present invention to provide a prefilled syringe of a before-use dissolving type which does not require a bypass passage defined by a recessed inner surface portion of an outer cylinder thereof, and includes a first containing portion and a second containing portion to which a liquid is transferred, wherein the second containing portion has a volume not less than a predetermined level so that a pressure difference occurring between the first containing portion and the second containing portion when a gasket is pushed in the outer cylinder for the transfer of the liquid is increased as compared with the conventional case to thereby reduce the administration preparatory period.

Solution to Problem

To achieve the object described above, the present invention has the following technical aspects:

A prefilled syringe of a before-use mixing type according to the present invention includes: an outer cylinder; a hollow needle provided in the outer cylinder as extending axially and having a cutting edge at its front end; a first gasket provided on a front side of the hollow needle in the outer cylinder; and a second gasket provided on a front side of the first gasket in the outer cylinder; wherein a first containing space is defined on a rear side of the first gasket in the outer cylinder for containing a liquid, and communicates with a rear end of the hollow needle. The syringe further includes: non-rotatively and complementarily shaped first and second engagement portions respectively provided at a front end of the first gasket and a rear end of the second gasket; wherein a second containing space is defined between the first gasket and the second gasket in the outer cylinder for containing a drug to be mixed with the liquid with a front end face of the first engagement portion and a rear end face of the second engagement portion abutting against each other to keep the first and second engagement portions out of engagement with each other; wherein the hollow needle is moved axially relatively toward the first gasket to penetrate through the first gasket to cause the first containing space and the second containing space to communicate with each other through the hollow needle; wherein the first gasket and the second gasket are rotated relative to each other and moved axially toward each other, whereby the first and second engagement portions are brought into engagement with each other to reduce the volume of the second containing space.

According to the present invention, even if an external force acts on the first and second gaskets, the volume of the second containing space defined between the first and second gaskets is not reduced with the front end face of the first engagement portion in abutment against the rear end face of the second engagement portion. Therefore, when the gaskets are pushed axially from one side or both sides of the first containing space to reduce the volume of the first containing space with the hollow needle penetrating through the first gasket to establish the communication between the first containing space and the second containing space, a greater internal pressure occurs in the first containing space, but does not occur in the second containing space. Therefore, the liquid can be smoothly transferred from the first containing space to the second containing space in a shorter period of time. After the liquid is transferred to the second containing space, the first gasket and the second gasket are rotated relative to each other and moved axially toward each other so as to bring the first and second engagement portions into engagement with each other. Thus, the volume of the second containing space is reduced, whereby the resulting liquid mixture drug flows out from the second containing space through a needle penetrating through the first gasket or the second gasket.

In the present invention, the syringe may be configured such that the second gasket is pushed rearward to push the first gasket rearward to reduce the volume of the first containing space. In this case, a plunger is preferably fixed to a front end of the second gasket, and the second gasket is preferably rotatably fitted in the outer cylinder.

Further, the syringe may be configured such that: the second gasket is fixedly provided in the outer cylinder; a third gasket is provided on the rear side of the first gasket in spaced relation to the first gasket in the outer cylinder to define the first containing space between the first gasket and the third gasket; and the volume of the first containing space is reduced by pushing the third gasket forward. In this case, the syringe may be configured such that: a plunger is fixedly provided on a rear side of the third gasket; the first and third gaskets are rotatably fitted in the outer cylinder; and the first and third gaskets are connected to each other so as to be rotated together when the volume of the first containing space is reduced to substantially zero.

According to another inventive aspect, a drug containing space is defined between the first and second gaskets which are rotated relative to each other to be brought into engagement with each other, and a liquid containing space is defined on the other side of the first gasket. This inventive aspect is applicable to prefilled syringes having various specific constructions. A preferred example of such a prefilled syringe is as follows:

A prefilled syringe of a before-use mixing type according to a preferred embodiment of the present invention includes: an outer cylinder; a hollow needle provided in the outer cylinder as extending axially and having a cutting edge at its front end; a first gasket provided on a front side of the hollow needle in an axially movable manner in the outer cylinder; a second gasket provided on a front side of the first gasket in an axially movable and rotatable manner in the outer cylinder; and a plunger to be operated for pushing the second gasket rearward; wherein a first containing space is defined on a rear side of the first gasket in the outer cylinder for containing a liquid, and communicates with a rear end of the hollow needle. The syringe further includes: non-rotatively and complementarily shaped first and second engagement portions respectively provided at a front end of the first gasket and a rear end of the second gasket; wherein a second containing space is defined between the first gasket and the second gasket in the outer cylinder for containing a drug to be mixed with the liquid with a front end face of the first engagement portion and a rear end face of the second engagement portion abutting against each other to keep the first and second engagement portions out of engagement with each other; wherein the second gasket is pushed rearward to move the first gasket rearward, whereby the hollow needle penetrates through the first gasket to cause the first containing space and the second containing space to communicate with each other through the hollow needle; wherein, when the second gasket is further pushed rearward to further move the first gasket rearward to reduce the volume of the first containing space, the hollow needle functions as a communication passage through which the liquid is transferred from the first containing space into the second containing space; wherein the second gasket is rotated relative to the first gasket and moved axially toward the first gasket, whereby the first and second engagement portions are brought into engagement with each other to reduce the volume of the second containing space.

With this arrangement, when the plunger is pushed rearward with the front end face of the first engagement portion in abutment against the rear end face of the second engagement portion, the first and second gaskets are moved rearward, whereby the hollow needle penetrates through the first gasket to establish the communication between the first and second containing spaces. When the plunger is thereafter further pushed rearward, the volume of the first containing space is reduced, whereby the liquid is transferred from the first containing space into the second containing space through the hollow needle. At this time, a greater internal pressure does not occur in the second containing space with the front end face of the first engagement portion in abutment against the rear end face of the second engagement portion, so that the transfer of the liquid is smoothly achieved in a shorter period of time. After the completion of the transfer of the liquid, the drug is sufficiently mixed with the liquid in the second containing space to prepare a liquid mixture drug. Then, the plunger is rotated to rotate the second gasket to a position which permits the engagement between the first and second engagement portions. After the second gasket is pierced with a second hollow needle or a front side of the first containing space is opened, the plunger is pushed, whereby the second gasket is moved rearward to reduce the volume of the second containing space. Thus, the liquid mixture drug can flow out from the second containing space to the outside through the hollow needle penetrating through the first or second gasket. This arrangement simplifies the construction of the syringe and reduces the number of components without the need for the third gasket. A small amount of air is preferably contained together with the liquid in the first containing space. The presence of the air permits the forward movement of the first gasket to pierce the first gasket with the hollow needle.

In the present invention, the second gasket may be inserted into the outer cylinder in vacuum, whereby the second containing space is kept in vacuum. With this arrangement, when the first gasket is pierced with the hollow needle to establish the communication between the first and second containing spaces, the liquid can be sucked into the second containing space from the first containing space by a negative internal pressure of the second containing space. This further facilitates the transfer of the liquid. With the first engagement portion in abutment against the second engagement portion, the first and second gaskets are not moved toward each other during storage even if the second containing space is kept in vacuum. More preferably, when the first and second engagement portions abut against each other, the second containing space has a volume that is substantially equal to the sum of the volume of the liquid contained in the first containing space, the volume of the air contained in the first containing space, and the volume of the drug contained in the second containing space.

A gas which permits the first gasket and the hollow needle to move relatively toward each other to pierce the first gasket with the hollow needle may be contained together with the liquid in the first containing space. Examples of the gas include air and other gases (e.g., nitrogen) which are chemically stable with respect to the liquid and the drug.

The syringe may further include a double head needle (second hollow needle) provided on a front side of the second gasket. The double head needle is moved axially rearward toward the second gasket to penetrate through the second gasket, thereby functioning as an outlet passage through which the liquid mixture drug containing the liquid and the drug flows out from the second containing space. With this arrangement, the double head needle is kept axially away from the second gasket during the storage. After the liquid is transferred into the second containing space to be mixed with the drug, the second gasket is pierced with the double head needle and the outer cylinder is pushed axially toward the second gasket, whereby the liquid mixture drug can flow out to the outside through the double head needle. In this arrangement, the outer cylinder preferably includes a rear end wall provided at a rear end thereof, and the hollow needle preferably includes a base plate integrally provided at a rear end thereof to be attached to an inner surface of the rear end wall, whereby the hollow needle is supported by the base plate as extending axially in the outer cylinder.

Further, the outer cylinder may have an attachment port provided at the rear end thereof for receiving an injection needle attachment, and the syringe may further include a cap removably attached to the attachment port to seal the attachment port, wherein, the rear end of the hollow needle communicates with the attachment port. With this arrangement, the liquid is transferred into the second containing space to be mixed with the drug, and the cap is removed from the attachment port to be replaced with the injection needle attachment. Then, a compressive force is applied to the second containing space, whereby the liquid mixture drug can flow out of the second containing space from the injection needle attachment through the hollow needle.

In the present invention, the term "mixing" is defined to include dissolving, suspending and dispersing, and further include preparation through a chemical reaction of the liquid and the drug after the mixing. The liquid may be a non-medicinal liquid. The liquid may be a liquid drug containing a medicinal component.

Advantageous Effects of Invention

According to the present invention, the syringe can be produced at higher mass productivity at lower costs without the need for employing an outer cylinder having a bypass passage defined by a recessed inner surface portion thereof. During the storage, the first and second engagement portions having complementary engagement structures abut against each other to be kept out of engagement, whereby the second containing space is defined between the first and second engagement portions. Therefore, the second containing space to which the liquid is transferred is allowed to have a volume not less than a predetermined level. Thus, when the gasket is pushed in to transfer the liquid, the pressure difference between the first containing space and the second containing space is increased to smoothly and speedily achieve the transfer of the liquid to thereby reduce the administration preparatory period.

DESCRIPTION OF EMBODIMENTS

Preferred embodiments of the present invention will hereinafter be described with reference to the drawings.

Figure 1:
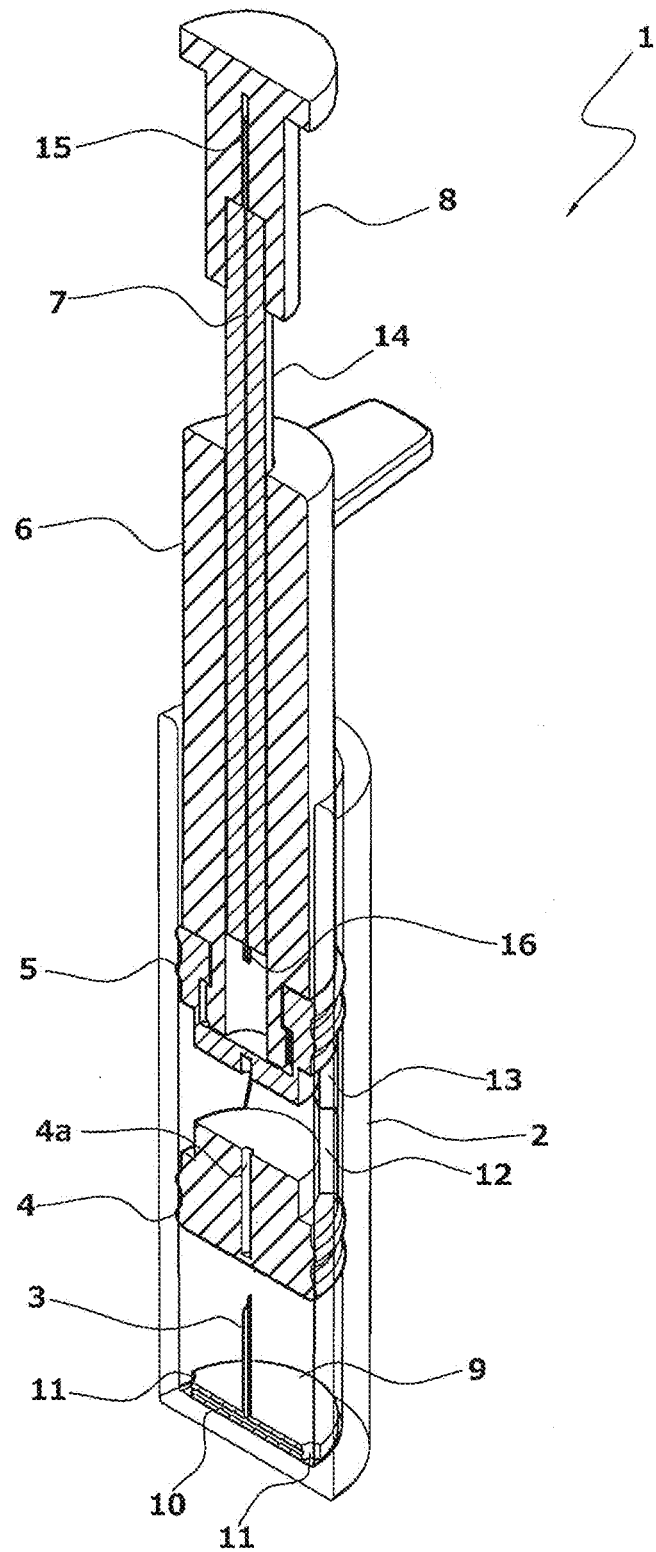
FIG. 1 is a perspective view in vertical section of a prefilled syringe according to a first embodiment of the present invention.

FIG. 1 illustrates a storage state of a prefilled syringe 1 of a before-use dissolving type according to a first embodiment of the present invention. The prefilled syringe 1 includes an outer cylinder 2 having a bottomed cylindrical shape and made of a transparent or translucent resin. In this patent application, the bottom side of the outer cylinder 2 is defined as "rear side" and the top side of the outer cylinder 2 is defined as "front side" for convenience of description, but these designations do not necessarily mean the front side and the rear side for the function of a product. In the figure, the internal construction is shown as seen through the outer cylinder 2.

The prefilled syringe 1 includes a hollow needle 3 extending axially in the outer cylinder 2 and having a cutting edge provided at a front end thereof, a first gasket 4 fitted in the outer cylinder 2 in an axially movable manner on a front side of the hollow needle 3, a second gasket 5 fitted in the outer cylinder 2 in an axially movable and rotatable manner on a front side of the first gasket 4, a plunger 6 to be operated for pushing the second gasket 5 rearward, an injection needle 7 which is a double head needle provided in the plunger 6 in an axially movable manner, and a safety cap 8 removably attached to a front portion of the injection needle 7. These components are disposed coaxially with each other.

The hollow needle 3 is provided integrally with a disk-shaped base plate 9 attached to an inner surface of a bottom wall (rear end wall) of the outer cylinder, and coaxially supported in the outer cylinder 2 by the base plate 9. The base plate 9 has a communication hole 10 extending diametrically therethrough and connected to an inner hole of the hollow needle 3 at its center, and notches 11 provided at opposite ends of the communication passage 10. Thus, a rear portion of the hollow needle 3 communicates with a space (first containing space) defined above the base plate 9.

The first gasket 4 is spaced a predetermined distance forward from the bottom wall of the outer cylinder 2 and the base plate 9, and the first containing space is defined by the first gasket 4, the bottom wall and the base plate 9 and the outer cylinder 2. A solvent (not shown) for dissolving a drug to be described later and air which permits the first gasket 4 to move rearward to be pierced with the front end of the hollow needle 3 are contained in the first containing space. For easy penetration of the hollow needle 3 through the first gasket 4, the first gasket 4 has a void 4a extending along a center axis thereof from a front end face thereof to a position adjacent to the rear end face thereof. The first gasket 4 has a thin wall portion at the axial center. The void 4a has an inner diameter that is substantially equal to the outer diameter of the hollow needle 3.

Non-rotatively and complementarily shaped first and second engagement portions 12, 13 engageable with each other without any gap are respectively provided at a front end of the first gasket 4 and a rear end of the second gasket 5. In the embodiment shown in FIG. 1, the first and second engagement portions 12, 13 have substantially the same structure, and each include a pair of projections diametrically opposed to each other and engagement recesses to be brought into engagement with the projections of the other engagement portion. The gaskets 4, 5 are made of a butyl rubber or other elastic material. The engagement portions 12, 13 may be each molded integrally with the corresponding gasket 4, 5 from the same material. However, the engagement portions 12, 13 (particularly, the projections) may be molded from a material different from that for the gaskets 4, 5, in this case, the engagement portion 12, 13 and the gasket 4, 5 may be integrally molded in the same mold, or may be separately molded and then fixed to each other by bonding, engaging, threading or other fixing method. The engagement portion 12, 13 may be molded from a harder material than the gasket 4, 5 (e.g., polypropylene, polytetrafluoroethylene or the like). Alternatively, the gasket 4, 5 may be molded integrally with the engagement portion 12, 13, and at least a surface portion of the resulting structure facing to the second containing space may be coated with a harder material for reinforcement of the engagement portion 12, 13. With this arrangement, where the second containing space is maintained in vacuum, the engagement portions 12, 13 are prevented from being flattened, so that a before-use mixing function can be ensured for a longer period of time.

In the storage state shown in FIG. 1, the second gasket 5 is fitted in the outer cylinder with the first and second engagement portions 12, 13 being rotatively offset about 90 degrees from each other to be kept out of engagement with each other. With a front end face of the first engagement portion 12 and a rear end face of the second engagement portion 13 in abutment against each other, the first and second engagement portions 12, 13 are prevented from being engaged with each other. Thus, a second containing space is defined between the first gasket 4 and the second gasket 5 in the outer cylinder 2. A powdery drug (not shown) to be dissolved in the solvent is contained in the second containing space.

Preferably, a drug filling step and a second gasket inserting step may be performed in vacuum. Thus, the second gasket 5 can be inserted into the outer cylinder in vacuum, so that the second containing space can be kept in vacuum. The drug may be a drug freeze-dried in the second containing space. In the storage state, the volume of the second containing space is substantially equal to the sum of the volume of the drug, the volume of the solvent and the volume of the air contained in the first containing space.

Figure 6:
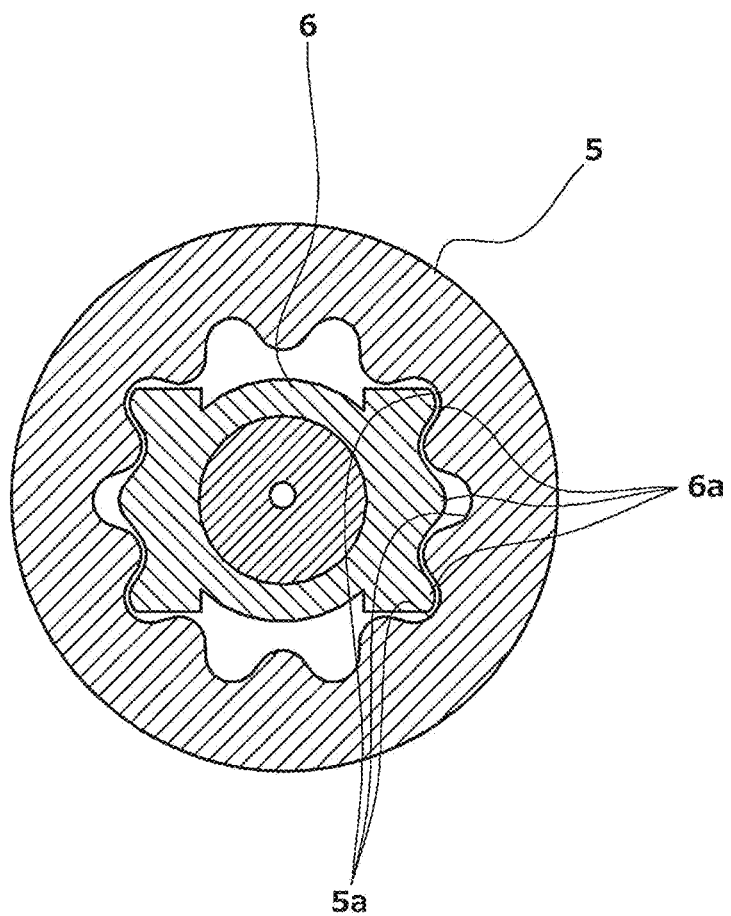
FIG. 6 is a cross sectional view showing an arrangement for engagement between a second gasket and a plunger of the prefilled syringe.

The plunger 6 is fixedly attached to the second gasket 5 so as to be non-rotatable relative to the second gasket 5. The attachment structure is not limited to a specific structure. In this embodiment, as shown in FIG. 6, the plunger 6 includes engagement projections 6a provided at a front end thereof as projecting diametrically. The second gasket 5 includes engagement recesses 5a provided in an inner peripheral surface thereof to be engaged with the engagement projections 6a for prevention of the relative rotation.

The plunger 6 has a flange 6b provided at a front end thereof for a plunging operation of the plunger 6. The plunger 6 has an axially extending hollow inner space, and the injection needle 7 is fitted in the plunger 6 in an axially movable manner.

The injection needle 7 includes an elongated main portion 14 fitted in the inner space of the plunger 6, and needle portions 15, 16 provided at axially opposite ends of the main portion 14. The needle portions 15, 16 each have a cutting edge at a tip thereof.

The cap 8 covers the front needle portion 15 of the injection needle 7 during the storage of the syringe, and functions as an operation portion which is operated for pushing the injection needle 7 into the plunger 6 for use of the syringe.

Next, an operation to be performed in the aforementioned embodiment will be described.

Figure 2:
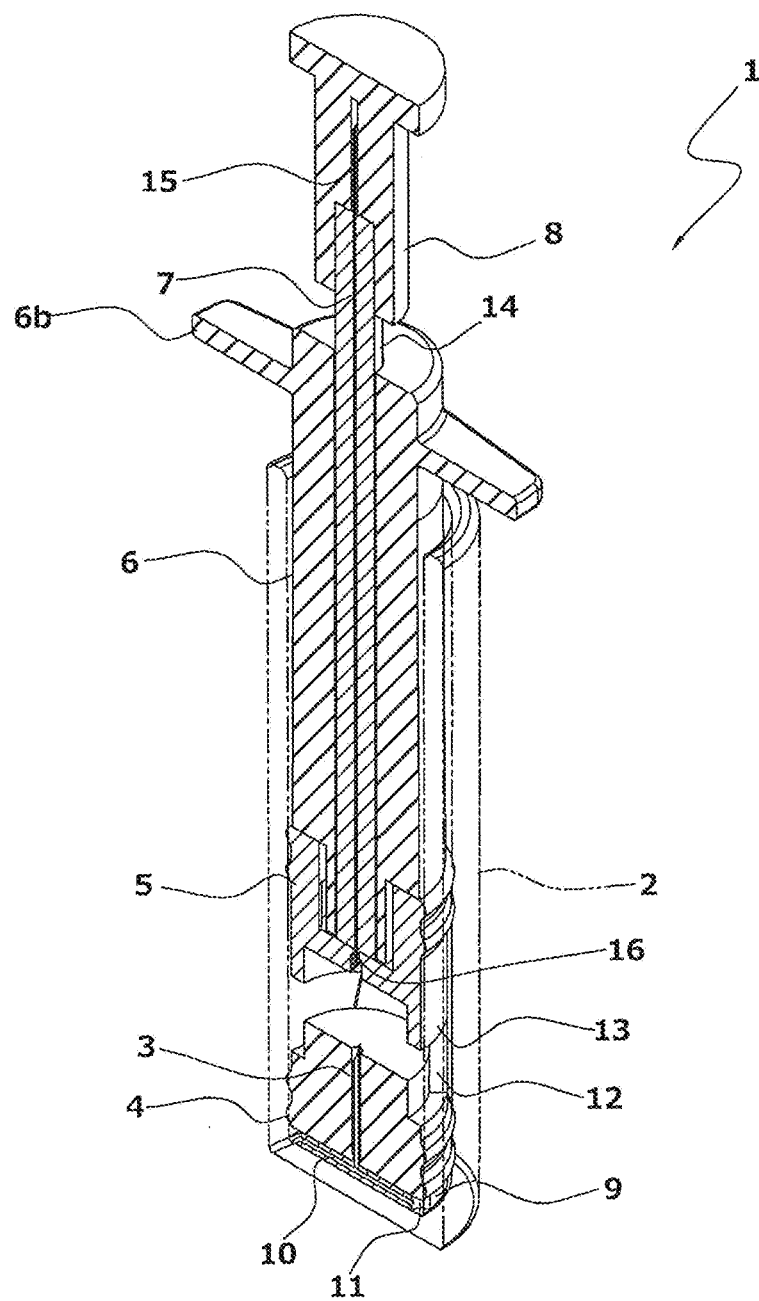
FIG. 2 is a diagram for explaining the operation of the prefilled syringe.

In the storage state, the drug is contained in the second containing space defined between the first and second gaskets 4, 5 with higher sealability and therefore, the efficacy of the drug can be properly maintained during prolonged storage. For use, the plunger 6 is pushed rearward. Thus, the second gasket 5 and the first gasket 4 are correspondingly pushed rearward without reduction in the volume of the second containing space. When the center thin wall portion of the first gasket 4 is pierced with the front end of the hollow needle 3, the first containing space and the second containing space communicate with each other through the inner hole of the hollow needle 3 and the communication hole 10 of the base plate 9. When the plunger 6 is further pushed rearward in this state to move the first gasket rearward, the volume of the first containing space is reduced to increase the internal pressure of the first containing space. Thus, the solvent is transferred from the first containing space into the second containing space through the inner hole (communication passage) of the hollow needle 3 (see FIG. 2).

Figure 3:
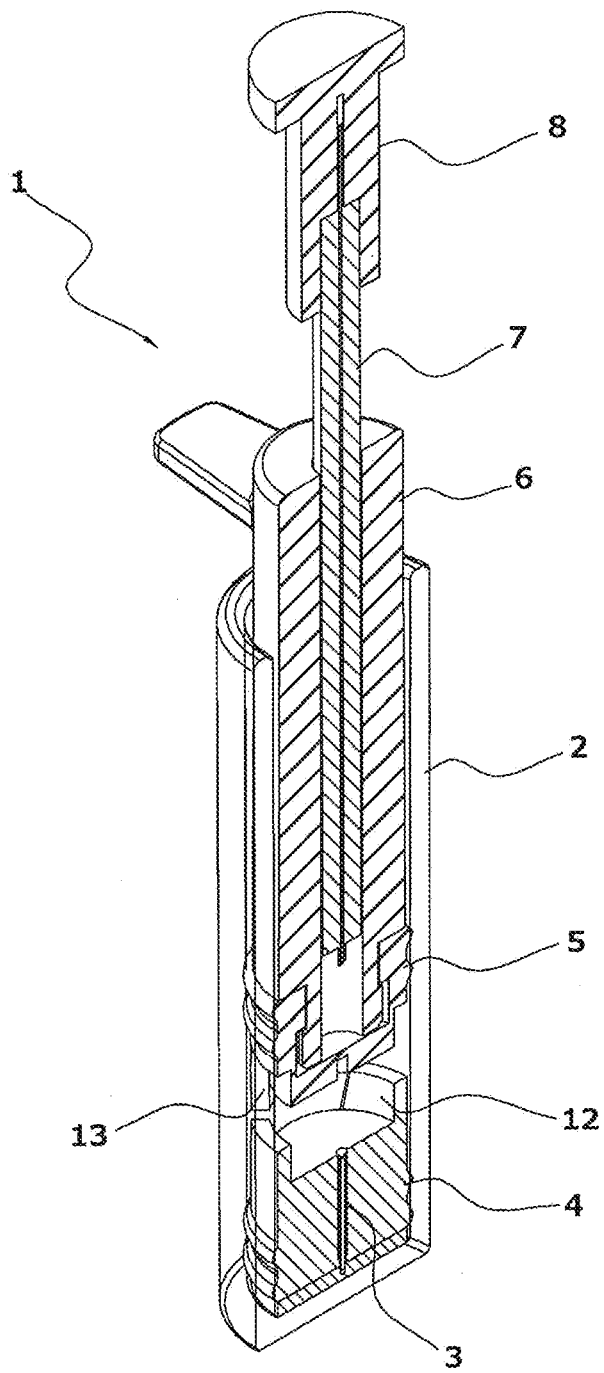
FIG. 3 is a diagram for explaining the operation of the prefilled syringe.

After the drug is sufficiently mixed with and dissolved in the solvent in the second containing space, the plunger 6 is rotated about 90 degrees with respect to the outer cylinder, whereby the second gasket 5 is rotated about 90 degrees with respect to the first gasket 4. Thus, the first and second engagement portions 12, 13 are located in engageable positions (see FIG. 3).

Then, the cap 8 is pushed in to push the injection needle 7 rearward. Thus, a center portion of the second gasket 5 is pierced with the rear needle portion 16, whereby the resulting drug solution can flow out from the second containing space through the injection needle 7.

Figure 4:
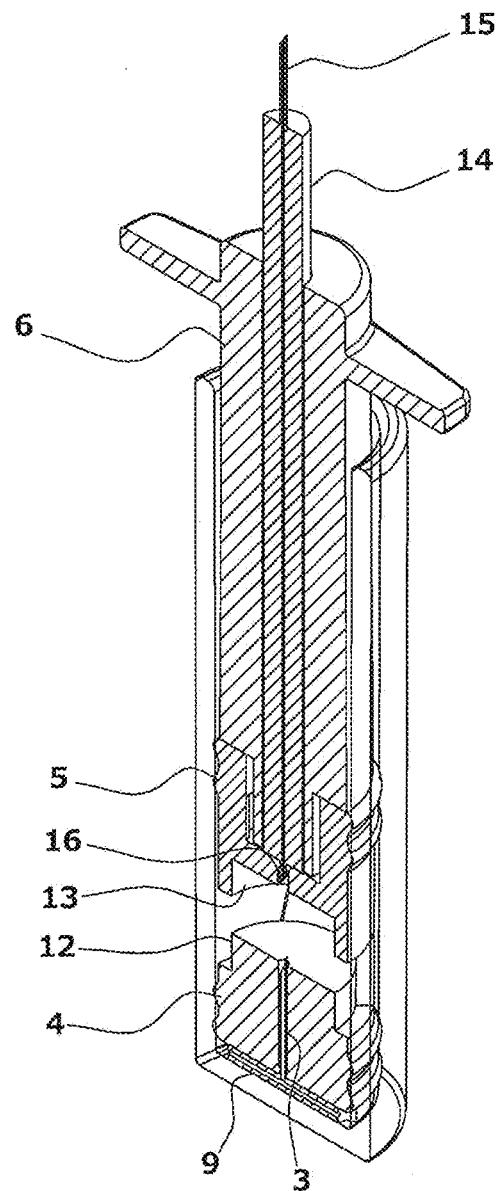
FIG. 4 is a diagram for explaining the operation of the prefilled syringe.
Figure 5:
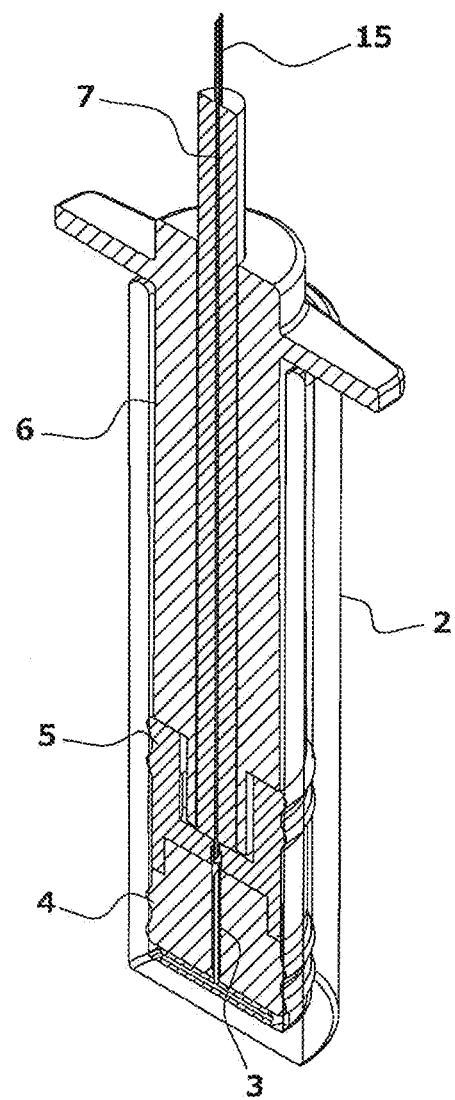
FIG. 5 is a diagram for explaining the operation of the prefilled syringe.

In this manner, the administration preparatory operation is completed. Then, as shown in FIG. 4, the cap 8 is removed from the injection needle 7 and, with the front needle portion 15 inserted in the patient, the plunger 6 is pushed forward. Thus, the second gasket 5 is pushed forward to reduce the volume of the second containing space, thereby increasing the internal pressure of the second containing space. Thus, the drug solution is administered into the patient from the second containing space through the injection needle 7. The plunger 6 is pushed to reduce the volume of the second containing space to substantially zero as shown in FIG. 5, whereby the predetermined amount of liquid drug can be reliably administered into the patient.

Figure 7:
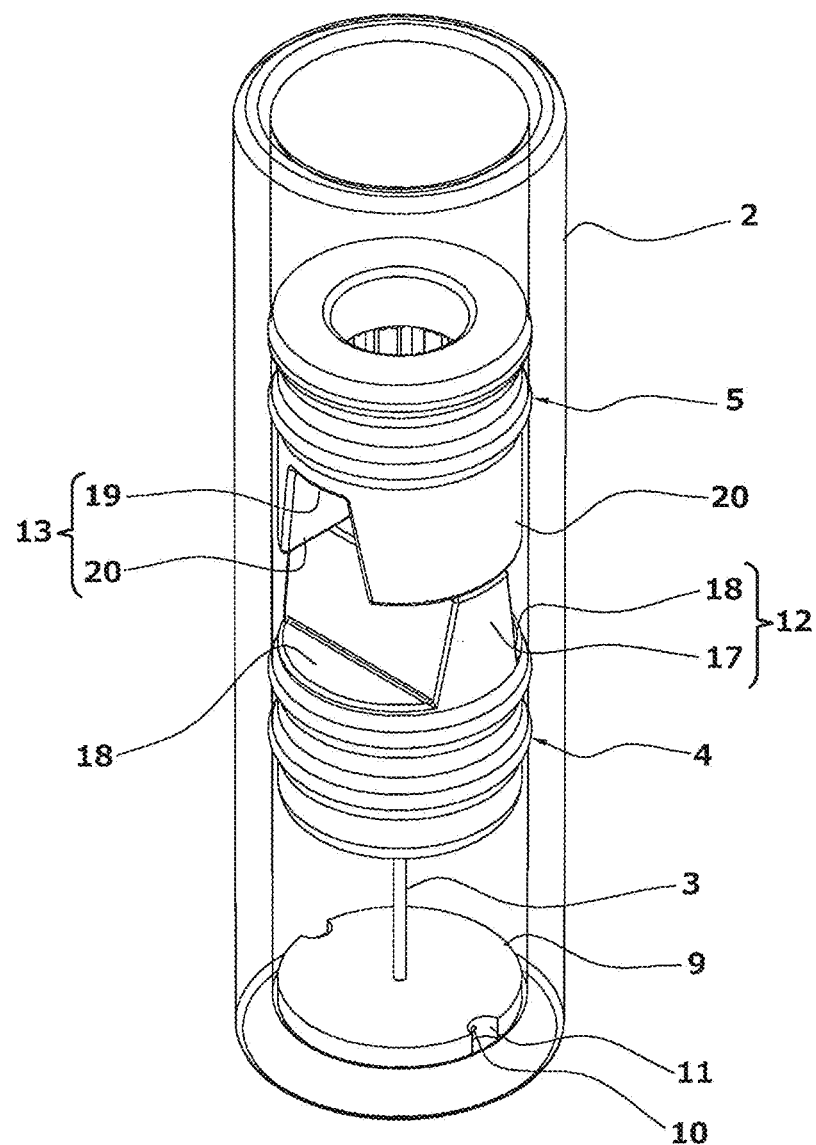
FIG. 7 is an enlarged perspective view showing a modification of first and second gaskets.
Figure 8:
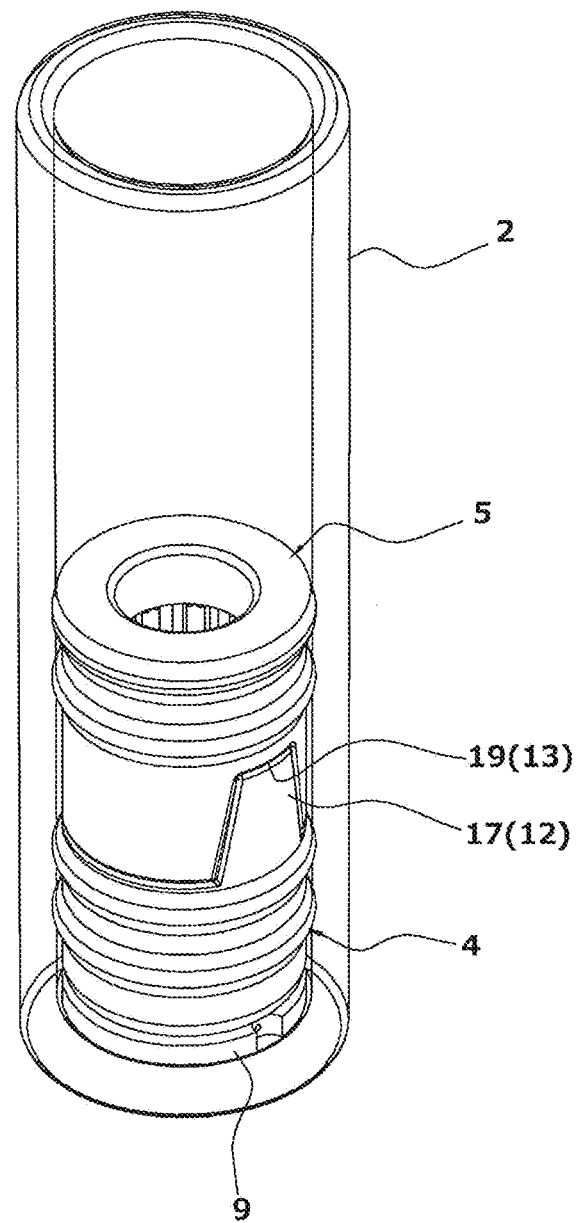
FIG. 8 is a diagram for explaining an operation to be performed in the modification.

FIGS. 7 and 8 show a modification of the first and second gaskets 4, 5. In this embodiment, the first engagement portion 12 of the first gasket 4 includes a diametrically extending projection 17 (projection), and recesses 18 (engagement recesses) provided on opposite sides of the projection 17. The second engagement portion 13 of the second gasket 5 includes a channel 19 (engagement recess) to be engaged with the projection 17, and projection walls 20 (projections) provided on opposite sides of the channel 19. In the storage state, as shown in FIG. 7, a front end face of the projection 17 of the first engagement portion 12 abuts against rear end faces of the projection walls 20 of the second engagement portion 13, whereby the second containing space is defined by the recesses 18 and the channel 19. After the completion of the administration, on the other hand, the first and second engagement portions are engaged with each other so as to reduce the volume of the second containing space to substantially zero as shown in FIG. 8.

FIGS. 9 to 26 illustrate a prefilled syringe 1 of a before-use dissolving type according to a second embodiment of the present invention. The first and second gaskets 4, 5 and the hollow needle 3 each have substantially the same function as in the first embodiment and, therefore, are designated by the same reference characters, and duplicate description will be omitted. Only different arrangements, different functions and different effects will be described in detail.

Figure 9:
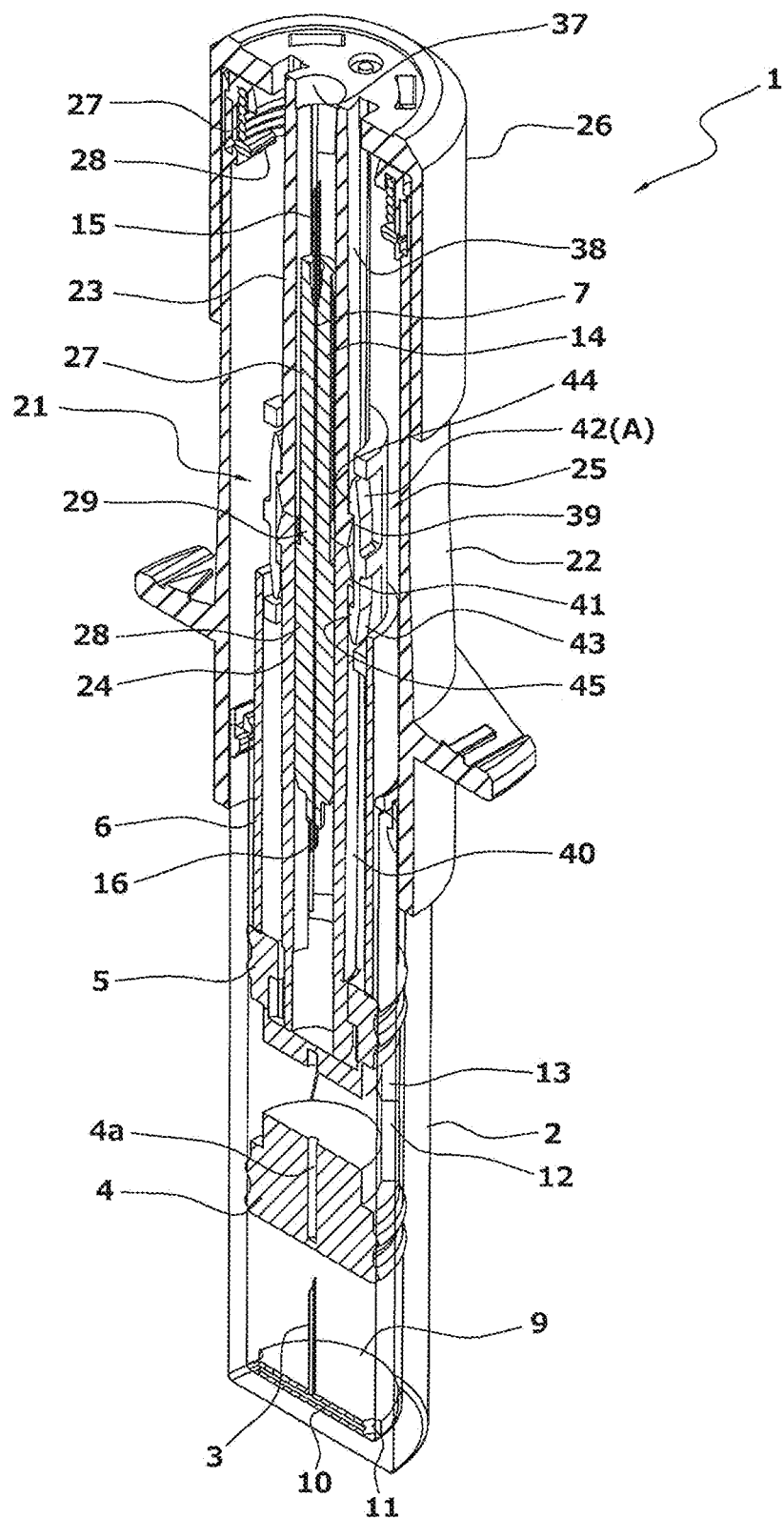
FIG. 9 is a perspective view in vertical section (X-Z section) of a prefilled syringe according to a second embodiment of the present invention.
Figure 10:
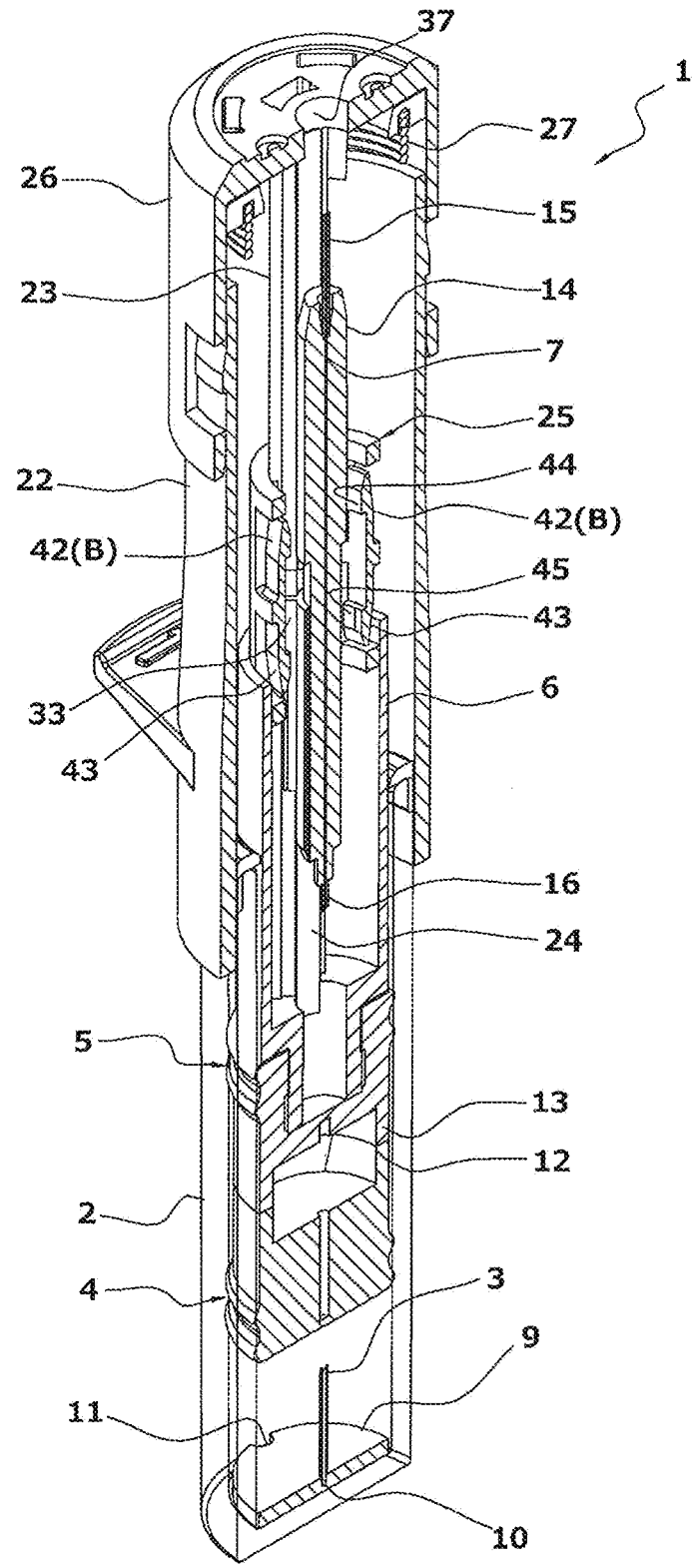
FIG. 10 is a perspective view in vertical section (Y-Z section) of the prefilled syringe.

In this embodiment, a safety operation mechanism 21 for the plunger 6 and the injection needle 7 is provided for reliably preventing inadvertent and careless operations. An initial storage state of the prefilled syringe 1 according to this embodiment is shown in FIGS. 9 and 10. The operation mechanism 21 of the prefilled syringe 1 of this embodiment is connected to a front end of the plunger 6. The operation mechanism 21 is operated in predetermined manners to push and rotate the plunger 6, to push the injection needle 7 and to lock the components.

The operation mechanism 21 includes a cylindrical operation cylinder 22 fitted around the outer cylinder 2 in an axially movable and rotatable manner, a pair of first connection rods 23 provided integrally with the operation cylinder 22, a pair of second connection rods 24 provided integrally with the plunger 6, and a key cylinder 25 fitted around the first and second connection rods 23, 24.

The first connection rods 23 may be provided integrally with the operation cylinder 22 but, in this embodiment, is provided integrally with a safety cap 26 fixed around a front portion of the operation cylinder 22. A spring 27 and a retention rib 28 retaining the spring 27 in an axially compressed state are provided in the cap 26. When the operation cylinder 22 is fully pushed toward the outer cylinder 2, the retention rib 28 abuts against a front end of the outer cylinder 2 to be detached from the cap 26. Thus, the spring 27 is released, whereby the cap 26 and the operation cylinder 22 are forcibly moved forward (axially upward) from a position shown in FIG. 26 by the spring 27. Thus, the front needle portion 15 of the injection needle 7 is accommodated in the cap 26.

Figure 11:
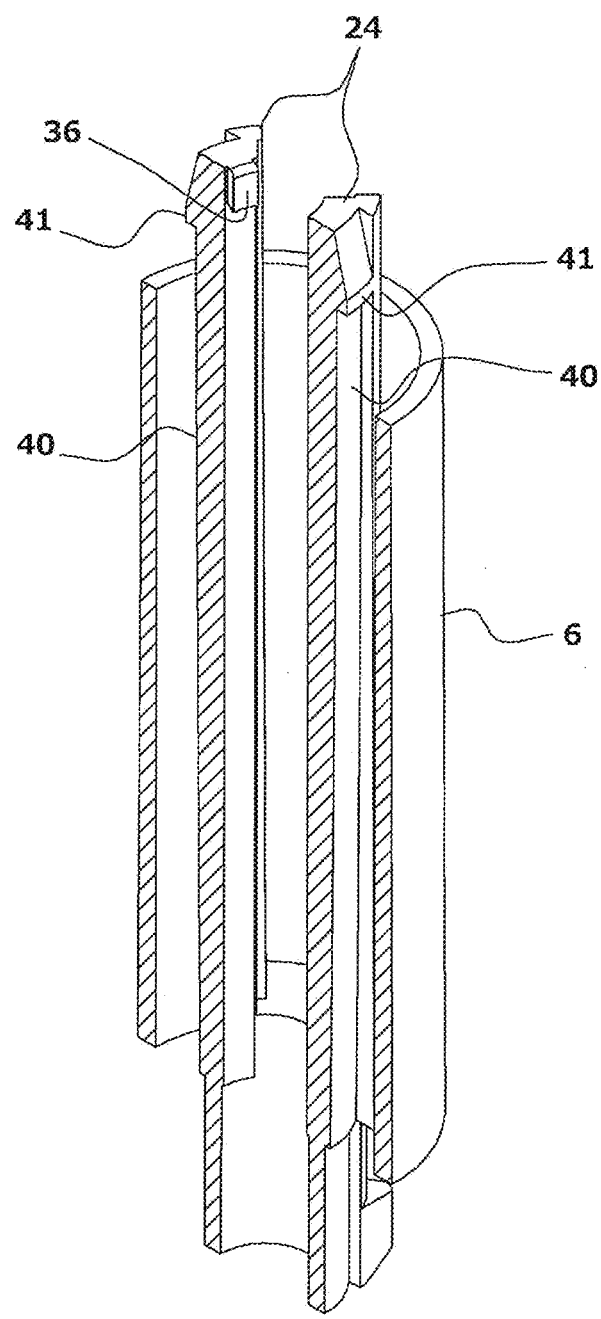
FIG. 11 is a perspective view in vertical section (X-Z section) of a plunger of the prefilled syringe.
Figure 12:
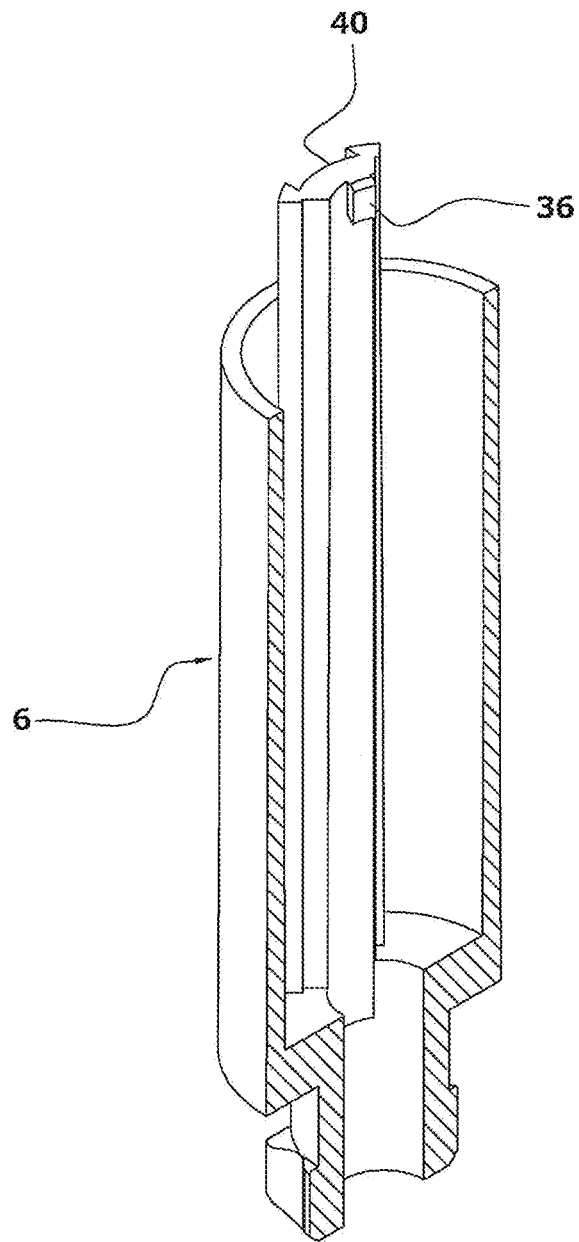
FIG. 12 is a perspective view in vertical section (Y-Z section) of the plunger of the prefilled syringe.
Figure 16:
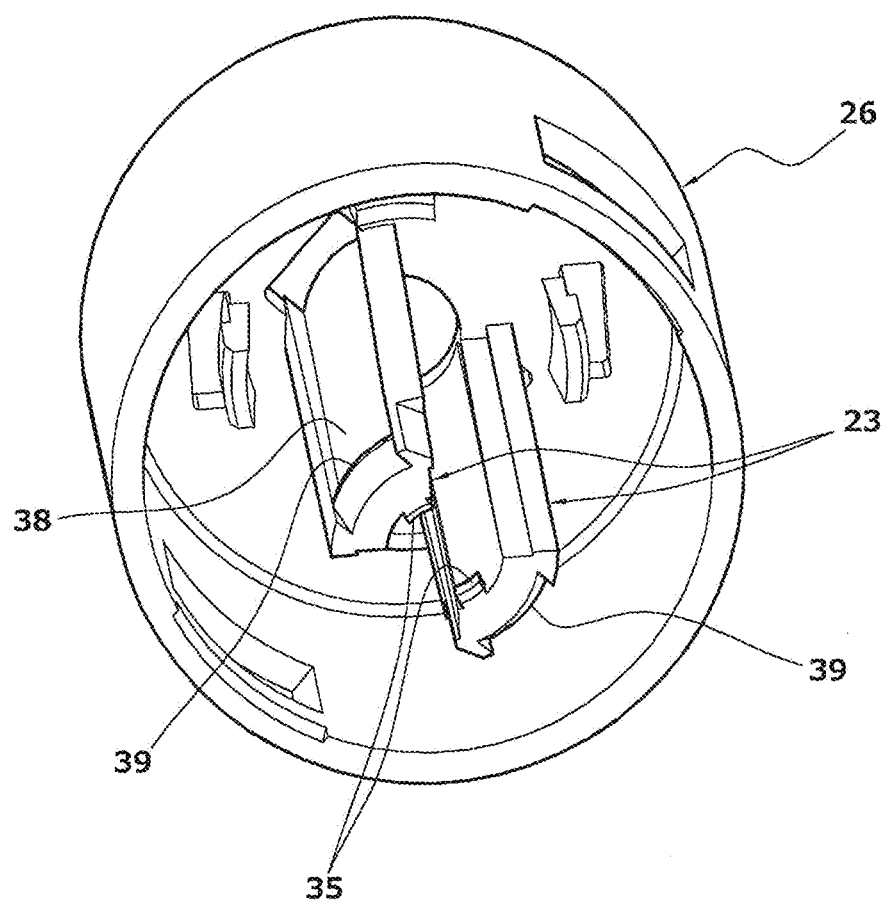
FIG. 16 is a perspective view of a safety cover of the prefilled syringe.

As shown in FIGS. 11, 12 and 16, the first and second connection rods 23, 24 are configured such that a pair of axially elongated members each having an arcuate cross section are diametrically opposed to each other. In the state shown in FIG. 9, rear end faces of the first connection rods 23 abut against front end faces of the second connection rods 24, whereby the operation cylinder 22 is prevented from being pushed toward the plunger 6. By rotating the first connection rods 23 counterclockwise about 90 degrees with respect to the second connection rods 24, on the other hand, the first connection rods 23 are positioned in spaces in which the second connection rods 24 are absent as seen axially in FIG. 23. Thus, the first connection rods 23 can be pushed axially toward the second connection rods 24.

Figure 17:
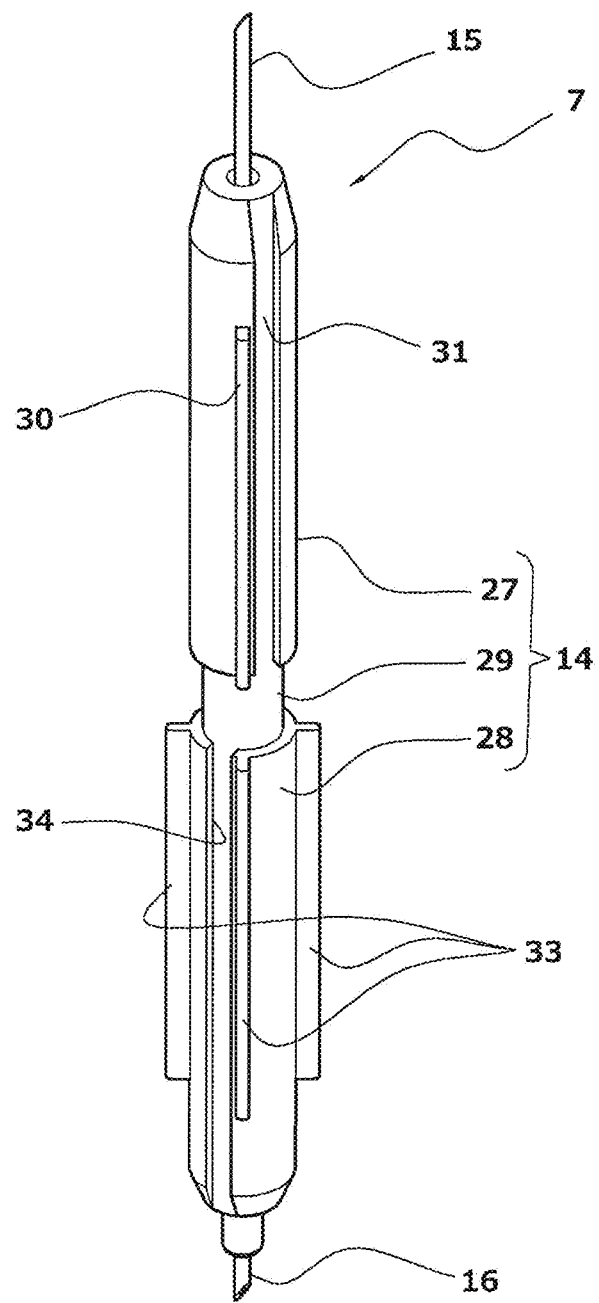
FIG. 17 is a perspective view of an injection needle of the prefilled syringe.

As shown in FIG. 17, the main portion 14 of the injection needle 7 includes a front first axial portion 27 around which the first connection rods 23 are fitted during the storage, a rear second axial portion 28 around which the second connection rods 24 are fitted during the storage, and a smaller-diameter axial portion 29 provided between the first axial portion 27 and the second axial portion 28.

The first axial portion 27 includes a pair of restriction ribs 30 provided on an outer peripheral surface thereof in diametrically opposed relation, and a pair of grooves 31 provided on the outer peripheral surface thereof in diametrically opposed relation as extending axially along the entire length thereof. The restriction ribs 30 permit the first connection rods 23 to rotate about 90 degrees relative to the first axial portion 27 but prevent the first connection rods 23 from rotating more than about 90 degrees relative to the first axial portion 27 in abutment against circumferential edges of the first connection rods 23. Further, the second axial portion 28 includes four restriction ribs 33 provided on an outer peripheral surface thereof, and a pair of grooves 34 provided in diametrically opposed relation as extending axially along the entire length thereof. The restriction ribs 33 abut against circumferential edges of the second connection rods 24 so as to prevent the second connection rods 24 from rotating relative to the second axial portion. The first connection rods 23 each have a projection key 35 provided on a rear portion of an inner surface thereof as shown in FIG. 16. The second connection rods 24 each have a projection key 36 provided on a front portion of an inner surface thereof as shown in FIGS. 11 and 12.

In the initial storage state, the keys 35, 36 are engaged with the smaller-diameter tubular portion 29. The keys 35 of the first connection rods 23 are axially engaged with a step defined between the smaller-diameter tubular portion 29 and the first axial portion 27, and the keys 36 of the second connection rods 24 are axially engaged with a step defined between the smaller-diameter tubular portion 29 and the second axial portion 28, whereby the injection needle 7 is prevented from axially moving with respect to the first and second connection rods 23, 24. The keys 36 of the second connection rods 24 are axially opposed to the grooves 31 of the first axial portion 27 during the storage and, when the first connection rods 23 are rotated about 90 degrees, the injection needle 7 can be moved forward relative to the second connection rods 24. At this time, the keys 36 are axially moved in the grooves 31. On the other hand, the keys 35 of the first connection rods 23 are offset about 90 degrees from the grooves 34 of the second axial portion 28 during the storage and, when the first connection rods 23 are rotated about 90 degrees relative to the injection needle 7, the keys 35 are axially opposed to the grooves 34. Thus, the first connection rods 23 can be moved forward relative to the injection needle 7. At this time, the keys 35 are axially moved in the grooves 34.

Figure 24:
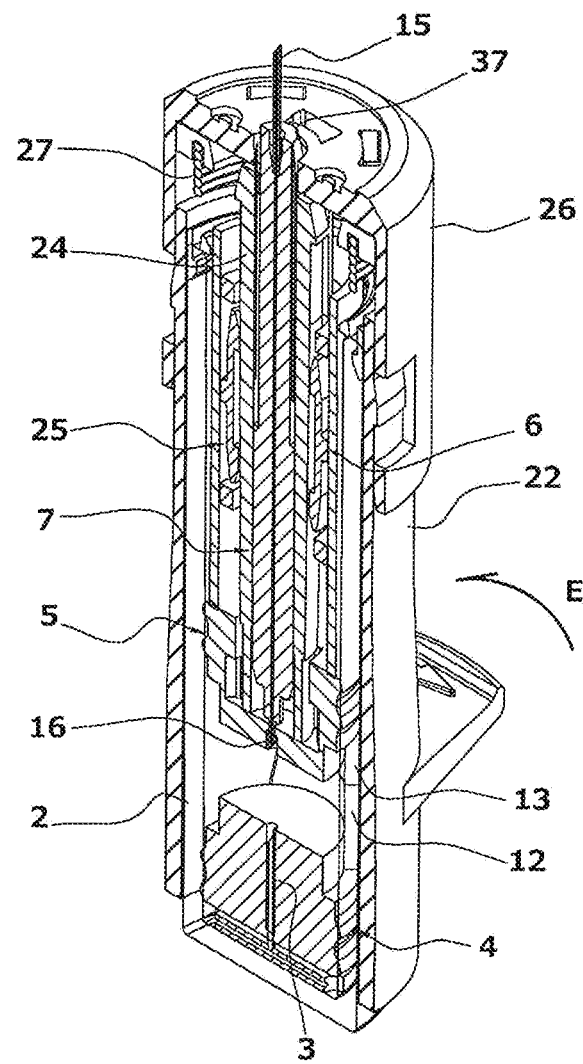
FIG. 24 is a diagram for explaining the operation of the prefilied syringe.
Figure 25:
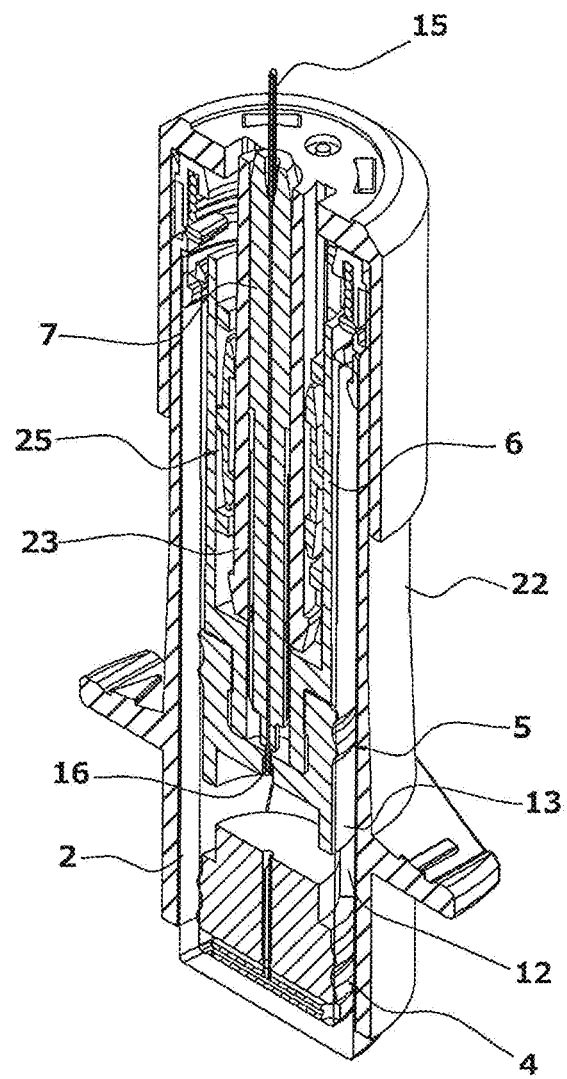
FIG. 25 is a diagram for explaining the operation of the prefilled syringe.
Figure 26:
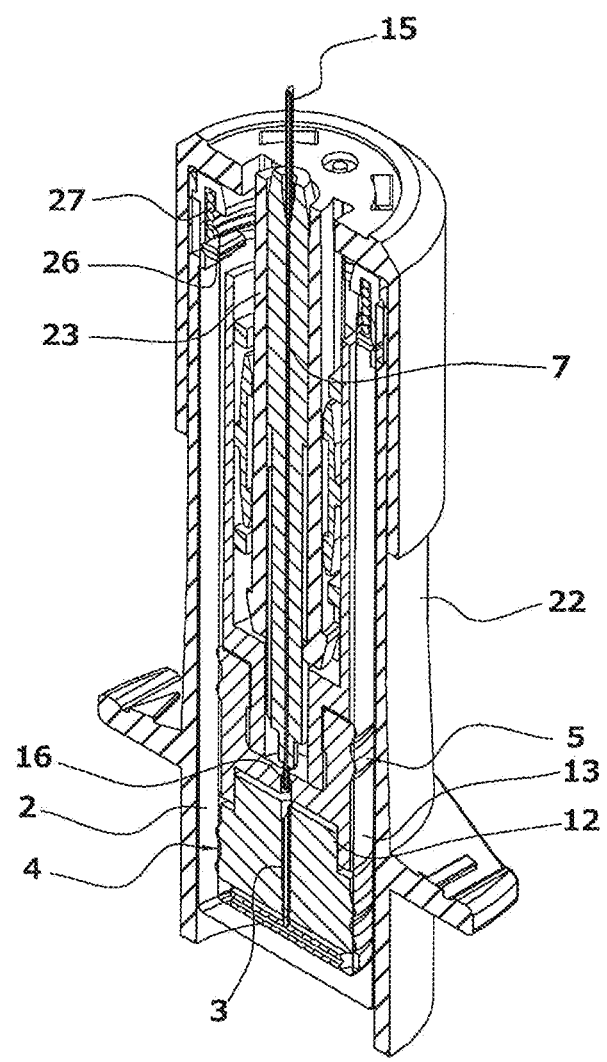
FIG. 26 is a diagram for explaining the operation of the prefilled syringe.

When the operation cylinder 22 is rotated 90 degrees with respect to the outer cylinder 2 from the initial state and pushed toward the outer cylinder 2, the first connection rods 23 are axially pushed toward the injection needle 7. As a result, as shown in FIG. 24, the front needle portion 15 of the injection needle 7 projects from a needle accommodating hole 37 of the safety cap 26. At this time, front portions of the restriction ribs 30 of the first axial portion 27 axially abut against the safety cap 26 around the needle accommodating hole 37. Thus, the injection needle 7 can be forcibly pushed rearward by the safety cap 26.

As shown in FIG. 16, the first connection rods 23 each have an engagement groove 38 provided on an outer peripheral surface thereof as extending axially, and an engagement projection 39 provided on a rear end (lower end) of the engagement groove 38. The engagement projection 39 has a generally horizontal step provided at a front end thereof. The engagement projection 39 has an outer surface tapered toward an axial rear end thereof as having a progressively reduced radius. As shown in FIGS. 11 and 12, the second connection rods 24 each have an engagement groove 40 provided on an outer peripheral surface thereof as extending axially, and an engagement projection 41 provided on a front end (upper end) of the engagement groove 40. The engagement projection 41 has a generally horizontal step provided at a rear end thereof. The engagement projection 41 has an outer surface tapered toward an axial front end thereof as having a progressively reduced radius. These engagement grooves 38, 40 are respectively engaged with engagement pieces 42, 43 of the key cylinder 25.

Figure 13:
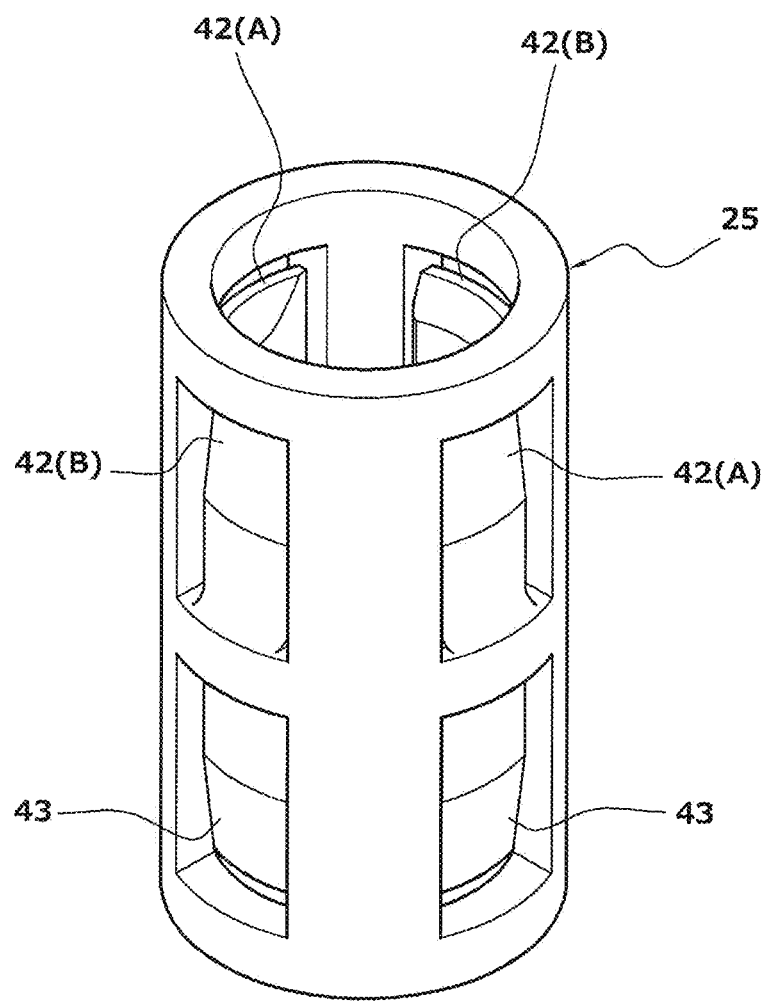
FIG. 13 is a perspective view of a key cylinder of the prefilled syringe.

The key cylinder 25 has a generally hollow cylindrical shape as shown in FIG. 13, and has four engagement pieces 42 circumferentially arranged in an upper (front) half region thereof, and four engagement pieces 43 circumferentially arranged in a lower (rear) half region thereof. The upper engagement pieces 42 extend forward from an axially middle portion of the key cylinder 25, and are resiliently deformable so that front edges of the engagement pieces 42 are radially expandable. The lower engagement pieces 43 extend rearward from the axially middle portion of the key cylinder 25, and are resiliently deformable so that rear edges of the engagement pieces 43 are radially expandable.

The upper engagement pieces 42 each have an engagement projection 44 provided on an inner surface thereof as having a step which is engaged with the engagement groove 38 of the first connection rod 23 in an axially movable and relatively non-rotatable manner and engaged with the engagement projection 39 from the front side. The engagement projection 44 has an inner surface tapered toward an axial front end thereof as having a progressively increased radius. The lower engagement pieces 43 each have an engagement projection 45 provided on an inner surface thereof as having a step which is engaged with the engagement groove 40 of the second connection rod 24 in an axially movable and relatively non-rotatable manner and engaged with the engagement projection 41 from the front side. The engagement projection 45 has an inner surface tapered toward an axial rear end thereof as having a progressively increased radius.

The tapered surfaces permit the rear ends of the first connection rods 23 to axially move over the lower engagement pieces 43 of the key cylinder 25, and permit the front ends of the second connection rods 24 to axially move over the upper engagement pieces 42 of the key cylinder 25. On the other hand, the steps permit the rear ends of the first connection rods 23 to be axially engaged with the upper engagement pieces 42, and permit the front ends of the second connection rods 24 to be axially engaged with the lower engagement pieces 43.

Figure 14:
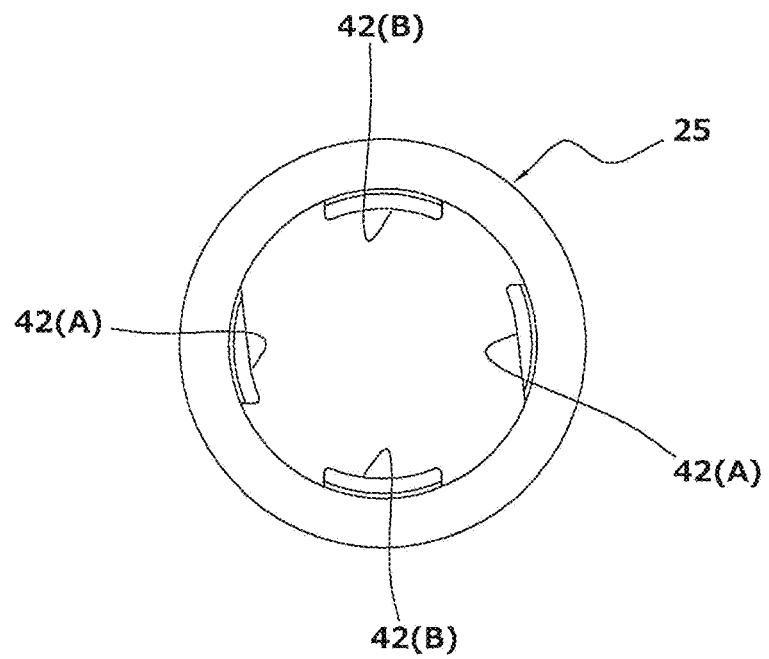
FIG. 14 is a plan view of the key cylinder.
Figure 20:
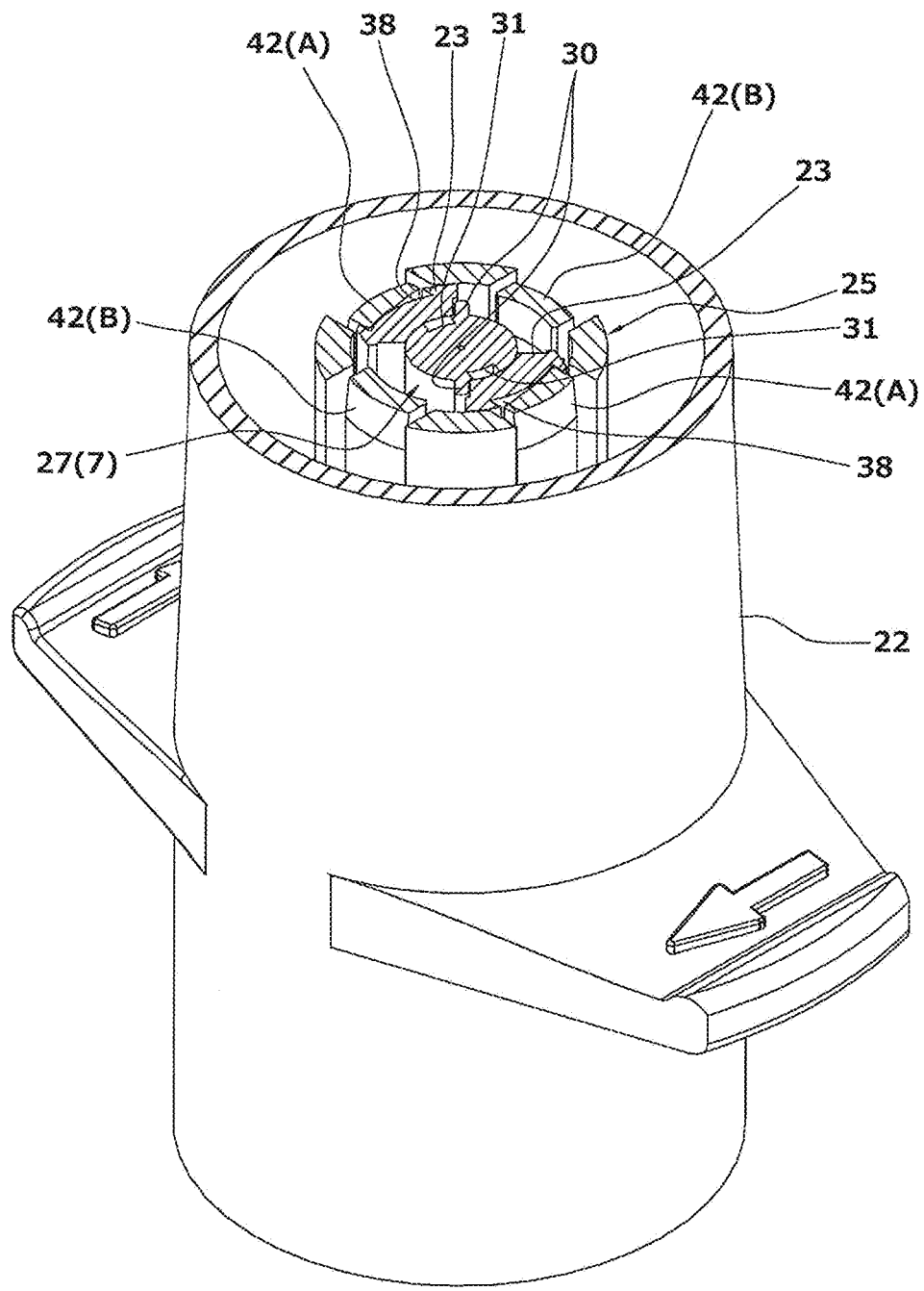
FIG. 20 is a perspective view in section taken along a line B-B in FIG. 18.

The first connection rods 23 are configured to be rotatable 90 degrees counterclockwise with respect to the key cylinder 25 from the position of the initial state, and to be locked at a 90-degree rotated position with respect to the rotation direction. More specifically, as shown in FIGS. 14 and 20, two engagement pieces 42A of the four upper engagement pieces 42 of the key cylinder 25 which are engaged with the engagement grooves 38 of the first connection rods 23 in the initial state each have an inner peripheral surface circumferentially tapered as having a diameter progressively increased in a clockwise direction. Thus, the engagement pieces 42A can be circumferentially detached from the engagement grooves 38 by rotating the first connection rods 23 counterclockwise with respect to the key cylinder 25. Further, the first connection rods 23 each have a tapered surface provided along an edge of the outer peripheral surface thereof with respect to the rotation direction (counterclockwise direction). Thus, when the first connection rods 23 are rotated, the other two engagement pieces 42B can be forced up into the engagement grooves 38 by the tapered edge surfaces. Inner peripheral surfaces of the other two engagement pieces 42B are not circumferentially tapered, so that the engagement pieces 42B cannot be circumferentially detached from the engagement grooves 38 after being engaged with the grooves 38.

Figure 15:
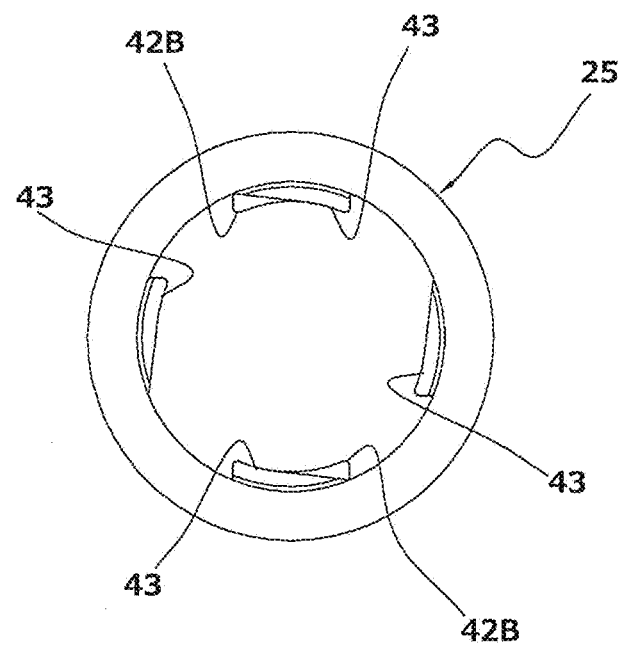
FIG. 15 is a bottom view of the key cylinder.
Figure 19:
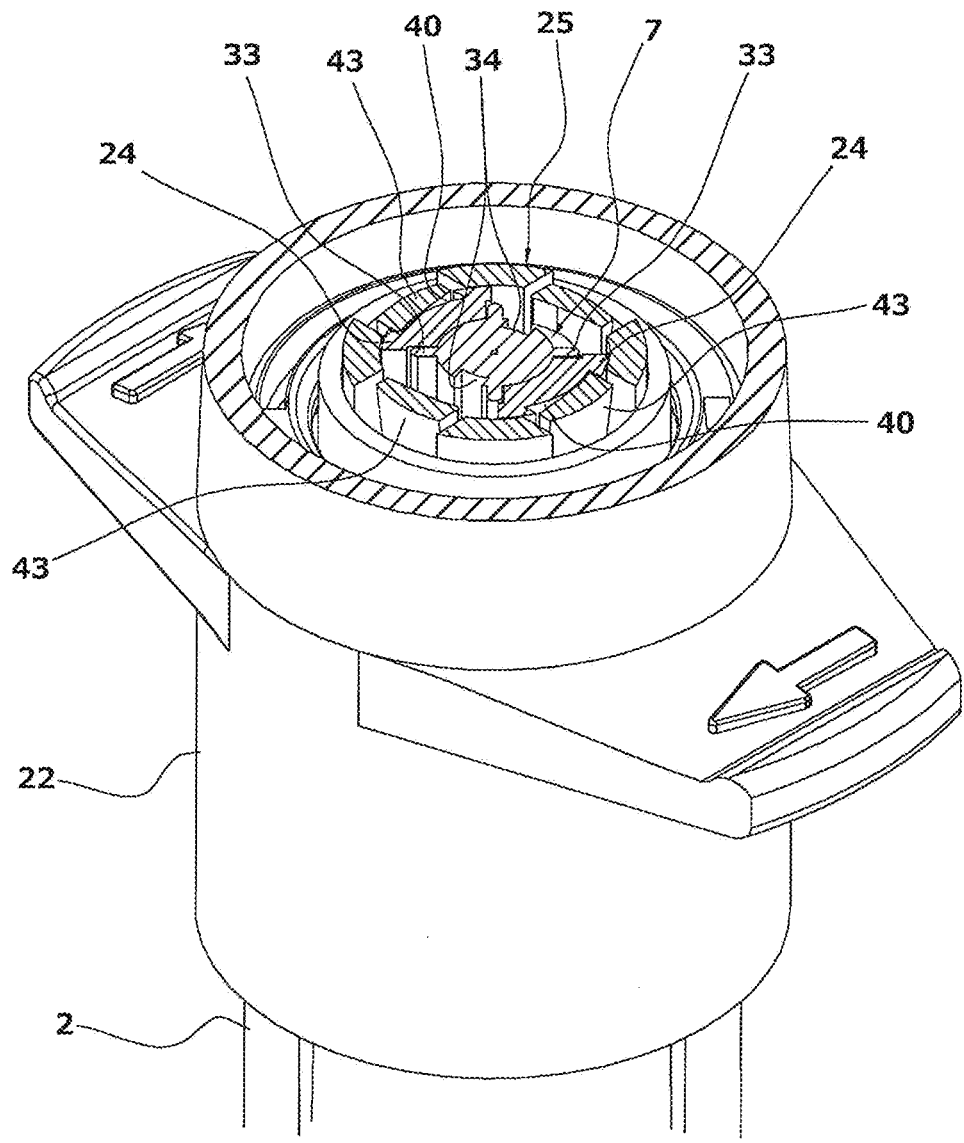
FIG. 19 is a perspective view in section taken along a line A-A in FIG. 18.

On the other hand, the key cylinder 25 is connected to the second connection rods 24 so as to be rotatable in one direction (clockwise). More specifically, as shown in FIGS. 15 and 19, the four lower engagement pieces 43 of the key cylinder 25 each have an inner peripheral surface tapered as having a diameter progressively increased in the clockwise direction. By rotating the key cylinder 25 clockwise with respect to the second connection rods 24, the engagement pieces 43 can be circumferentially disengaged from the engagement grooves 40 to be engaged with the next engagement grooves 40.

Next, the operation of the prefilled syringe 1 according to the second embodiment will be described.

Figure 18:
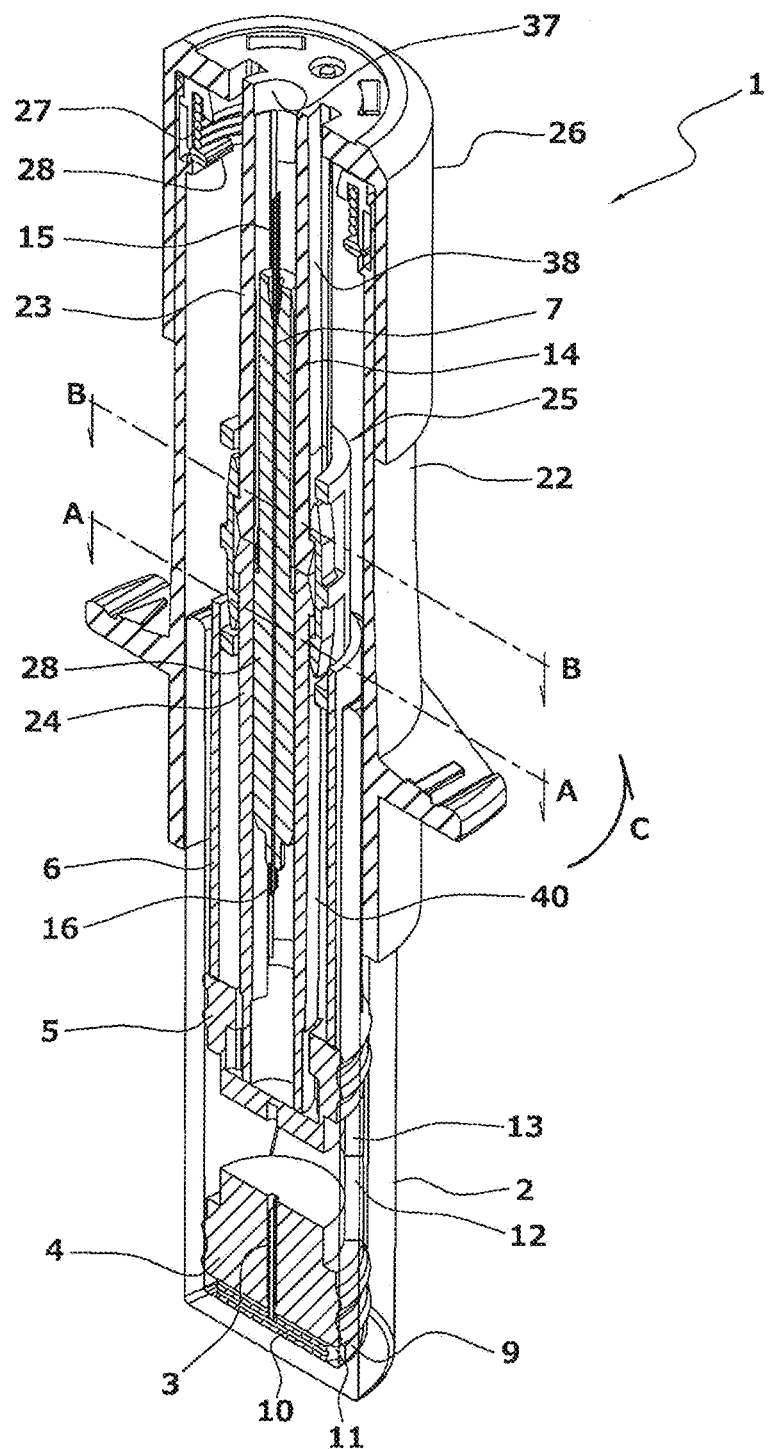
FIG. 18 is a diagram or explaining the operation of the prefilled syringe.

When the operation cylinder 22 is pushed rearward with respect to the outer cylinder 2 from the initial position shown in FIGS. 9 and 10 to a first operation position shown in FIG. 18, the plunger 6 is also pushed rearward with the first connection rods 23 in abutment against the second connection rods 24, whereby the second gasket 5 and the first gasket 4 are pushed rearward. Thus, the hollow needle 3 penetrates through the first gasket 4, and the liquid is transferred from the first containing space into the second containing space.

Then, the operation cylinder 22 is rotated counterclockwise (in an arrow direction C in FIG. 18) with respect to the outer cylinder 2. At this time, the rotation of the second connection rods 24 provided integrally with the plunger 6 are restricted by a fitting force with which the second gasket 5 is fitted in the outer cylinder 2. As shown in FIG. 19, the rotation of the injection needle 7 fitted in the second connection rods 24 is also restricted by the restriction ribs 33. Further, the lower engagement pieces 43 of the key cylinder 25 are engaged counterclockwise with and locked to the engagement grooves 40 of the second connection rods 24. On the other hand, as shown in FIG. 20, the first connection rods 23 are rotatable 90 degrees counterclockwise about the injection needle 7, and rotatable 90 degrees counterclockwise with respect to the key cylinder 25. Therefore, the first connection rods 23 are rotated 90 degrees with respect to the second connection rods 24, the injection needle 7 and the key cylinder 25.

Figure 21:
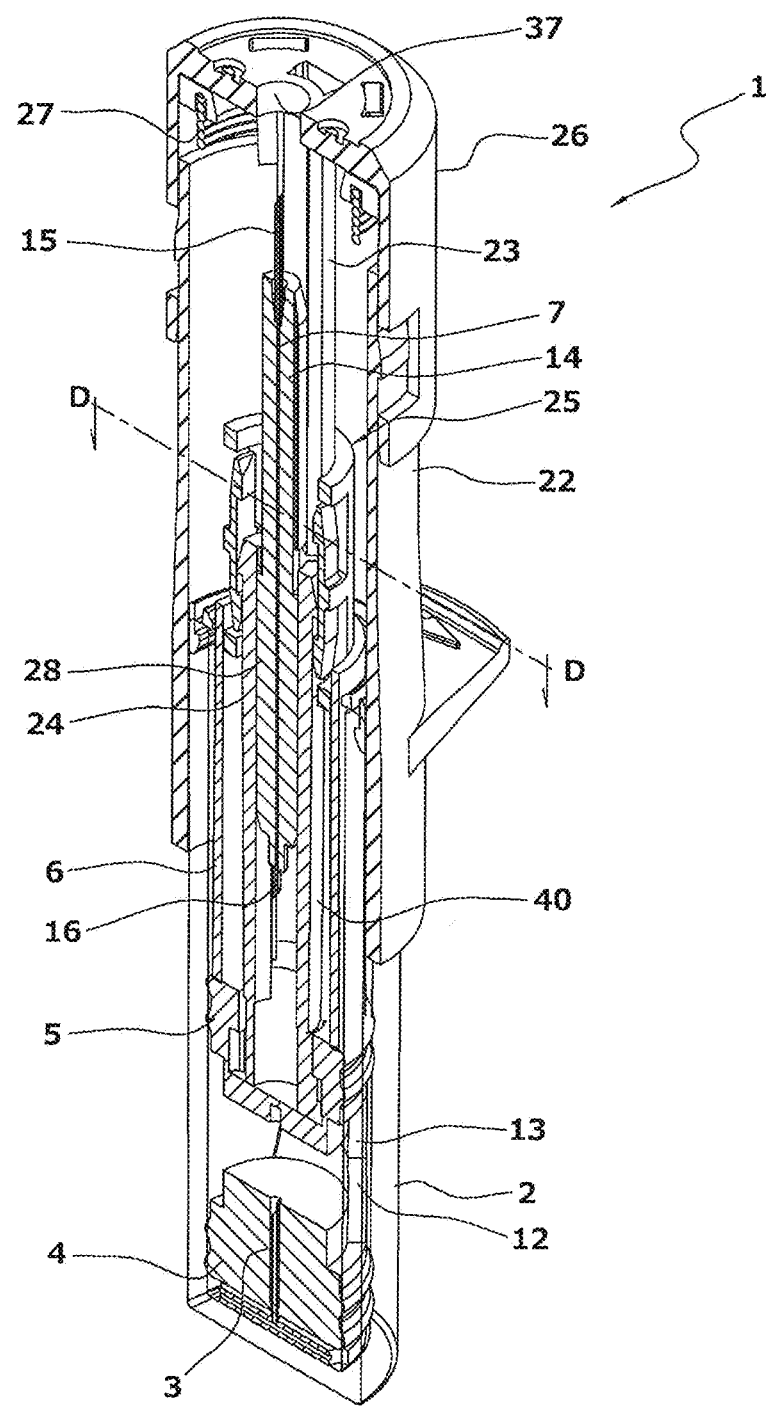
FIG. 21 is a diagram for explaining the operation of the prefilled syringe.
Figure 22:
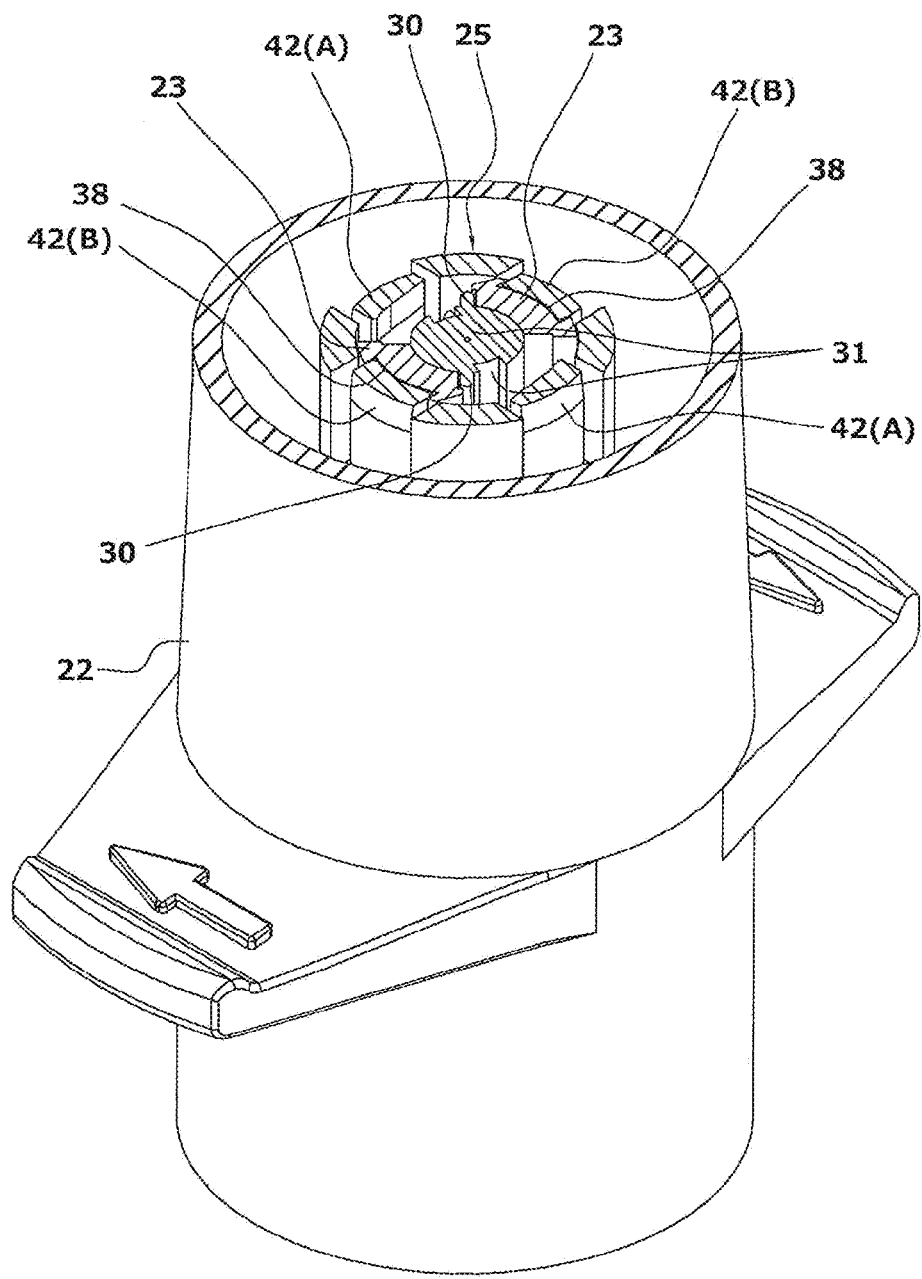
FIG. 22 is a perspective view in section taken along a line D-D in FIG. 21.
Figure 23:
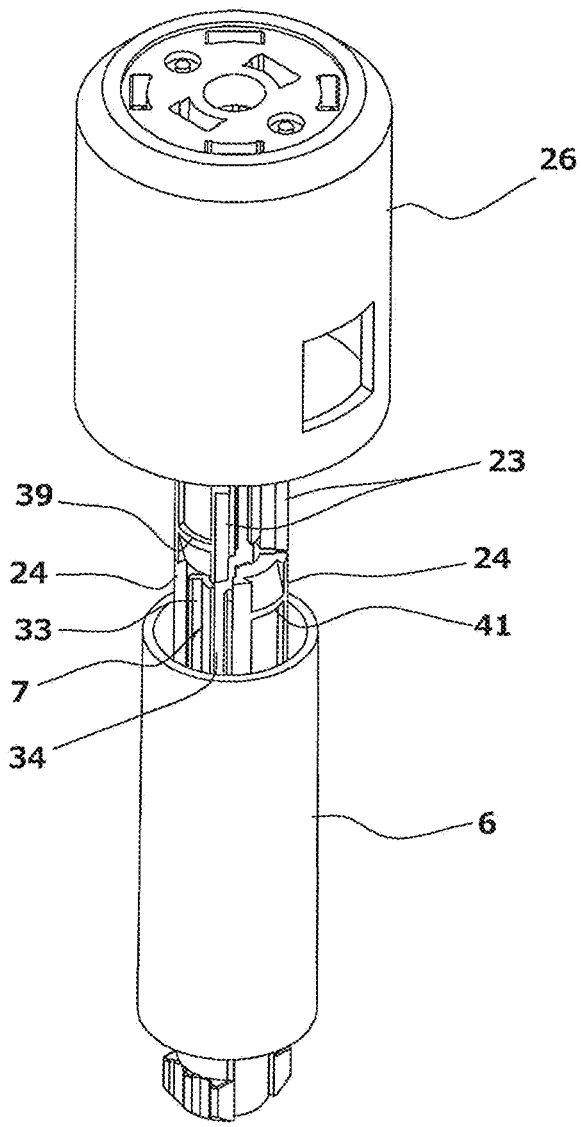
FIG. 23 is a perspective view showing the internal construction of the prefilled syringe shown in FIG. 21.

By this operation, the operation cylinder 22 is rotated to a second operation position shown in FIG. 21, whereby the first connection rods 23 and the key cylinder 25 are locked with respect to the rotation direction as shown in FIG. 22. At the second operation position, the first connection rods 23 are engageable with the second connection rods 24 as shown in FIG. 23. Further, the first connection rods 23 can be pushed rearward with respect to the injection needle 7, and the injection needle 7 can be pushed toward the second connection rods 24.

Subsequently, the operation cylinder 22 is pushed rearward to a third operation position shown in FIG. 24 with respect to the outer cylinder 2. At this time, the rear ends of the first connection rods 23 are axially moved over the lower engagement pieces 43 of the key cylinder 25, and the front ends of the second connection rods 24 are axially moved over the upper engagement pieces 42 of the key cylinder 25, whereby the key cylinder 25 is fitted around axially middle portions of the first and second connection rods 23, 24 which are engaged with each other in axially overlapping relation. Further, the injection needle 7 is also forcibly pushed rearward by the pushing of the operation cylinder 22, whereby the rear needle portion 16 penetrates through the second gasket 5. Thus, the liquid mixture drug can flow out through the injection needle 7.

Then, the operation cylinder 22 is rotated 90 degrees counterclockwise (in an arrow direction E). At this time, the second connection rods 24, the injection needle 7 and the key cylinder 25 are locked with respect to the first connection rods 23 in the rotation direction. Therefore, the second gasket 5 is rotated 90 degrees to a fourth operation position shown in FIG. 25 against a resistive force with which the second gasket 5 is fitted in the outer cylinder 2. At this time, the second gasket 5 is located at a position such as to be engageable with the first gasket 4. Thus, the administration preparatory operation is completed.

Then, the front needle portion 15 of the injection needle 7 is inserted in the patient, and the operation cylinder 22 is pushed toward the outer cylinder 2, whereby the liquid mixture drug is administered into the patient from the second containing space through the injection needle 7.

After the completion of the administration, the operation cylinder 22 and the safety cap 26 are urged forward away from the outer cylinder 2 by the released spring 27. Thus, the front needle portion 15 of the injection needle 7 is fully accommodated in the cap 26. It is noted that the operation cylinder 22 can be completely locked by lifting the operation cylinder 22 forward away from the second connection rods 24 and then rotating the operation cylinder 22 clockwise by 90 degrees.

Figure 27:
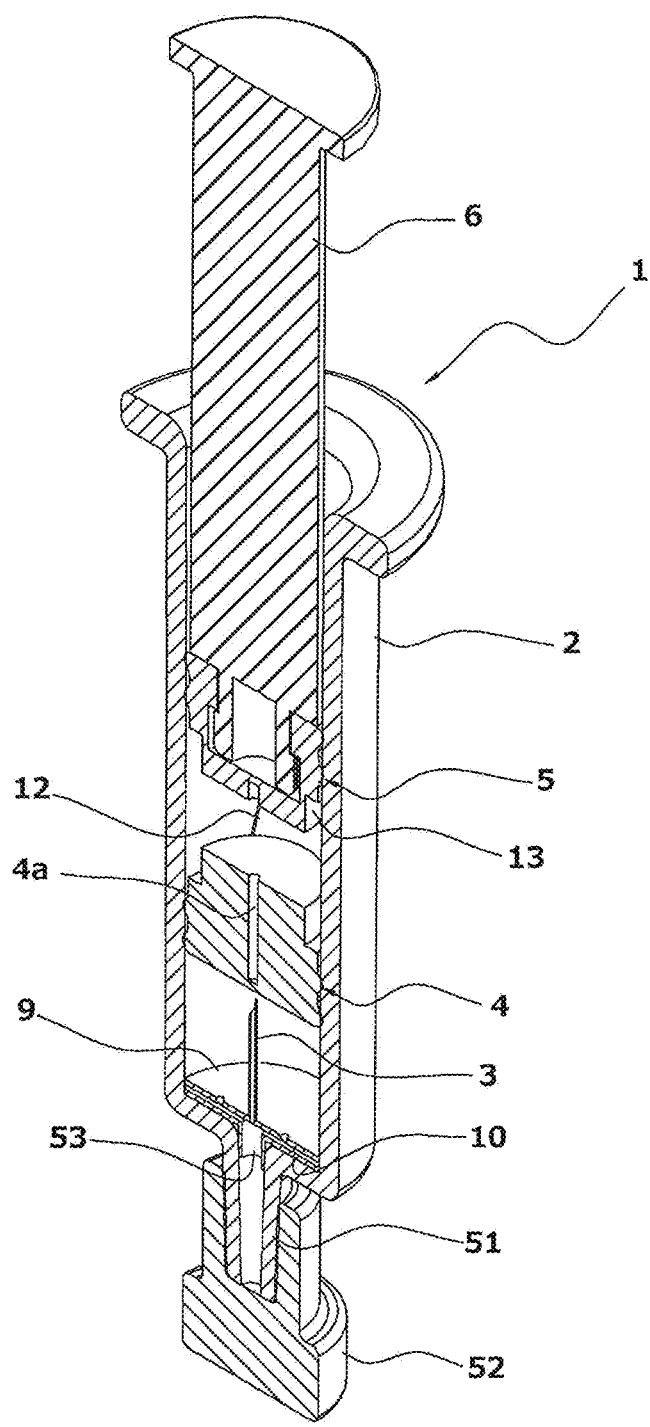
FIG. 27 is a perspective view in vertical section of a prefilled syringe according to a third embodiment of the present invention.
Figure 28:
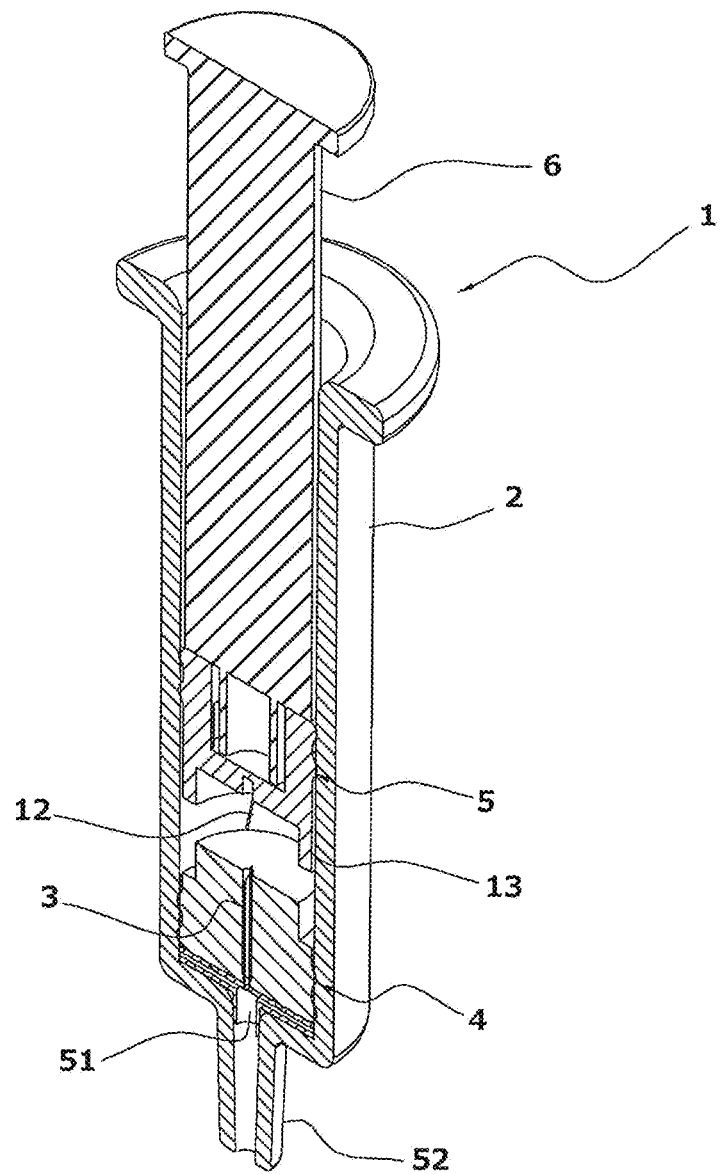
FIG. 28 is a diagram for explaining the operation of the prefilled syringe.
Figure 29:
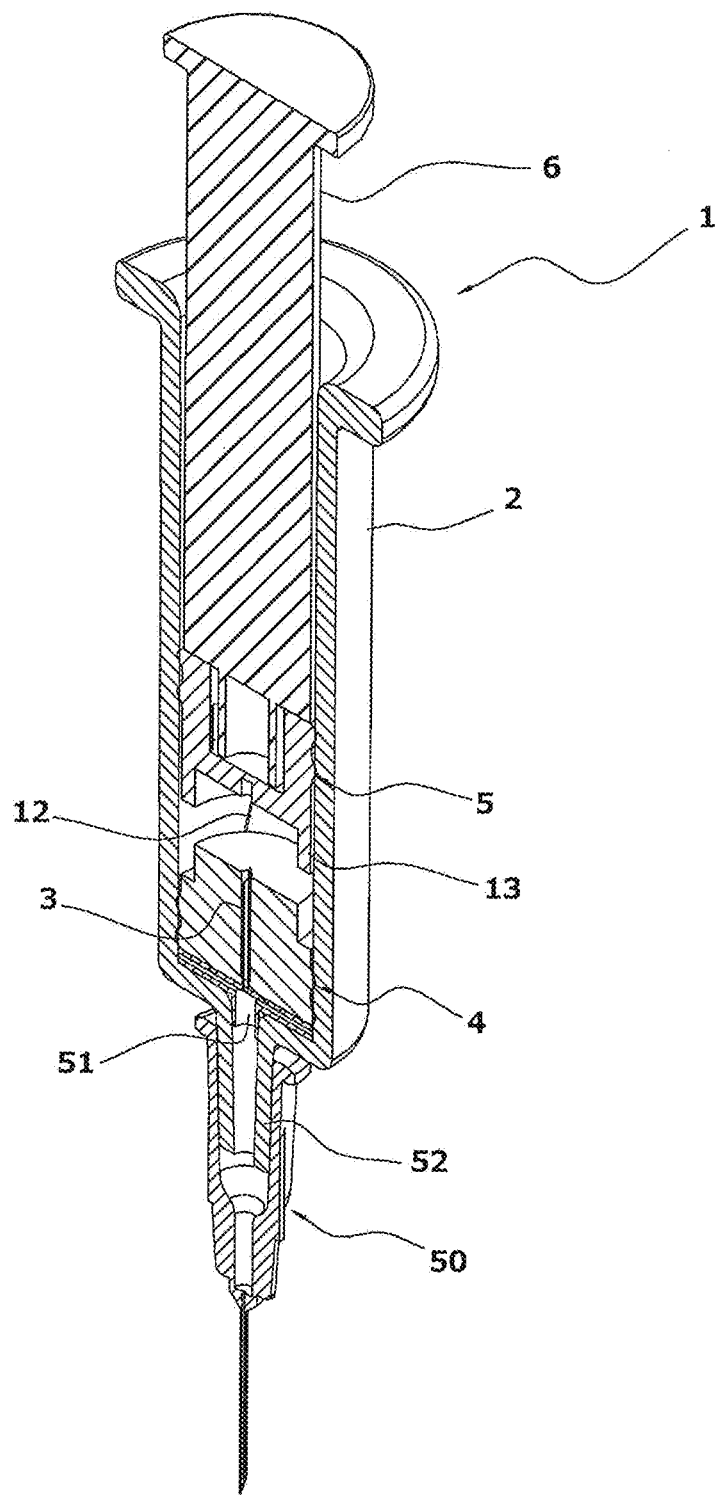
FIG. 29 is a diagram for explaining the operation of the prefilled syringe.

FIGS. 27 to 29 illustrate a prefilled syringe 1 of a before-use dissolving type according to a third embodiment of the present invention. Components corresponding to those in the first embodiment are designated by the same reference characters as in the first embodiment, and will not be described in detail. Only different arrangements, different functions and different effects will be described.

In this embodiment, the injection needle is not provided on the side of the plunger 6. The outer cylinder 2 has a cylindrical attachment port 51 provided at the rear end thereof for receiving an injection needle attachment 50, and a cap 52 is removably attached to a rear end of the attachment port 51 for closing the attachment port 51. The base plate 9 has a cylindrical outlet port 53 provided in a back surface (rear end face) thereof to communicate with the inner hole of the hollow needle 3, and the outlet port 53 is fitted in the attachment port 51.

When the liquid is to be transferred from the first containing space into the second containing space in this embodiment, the attachment port 51 is closed with the cap 52 as shown in FIG. 27. Thus, the liquid can be smoothly transferred into the second containing space while the liquid is prevented from flowing out from the attachment port 51. When the liquid mixture drug in the second containing space is to be administered into the patient, the cap 52 is removed as shown in FIG. 28, and the plunger 6 is rotated to bring the first and second gaskets 4, 5 into a mutually engageable state. Then, the injection needle attachment 50 is attached to the attachment port 51 as shown in FIG. 29. In turn, the plunger 6 is pushed rearward, whereby the liquid mixture drug flows back to the hollow needle 3 from the second containing space and flows out from the injection needle attachment 50.

Figure 30:
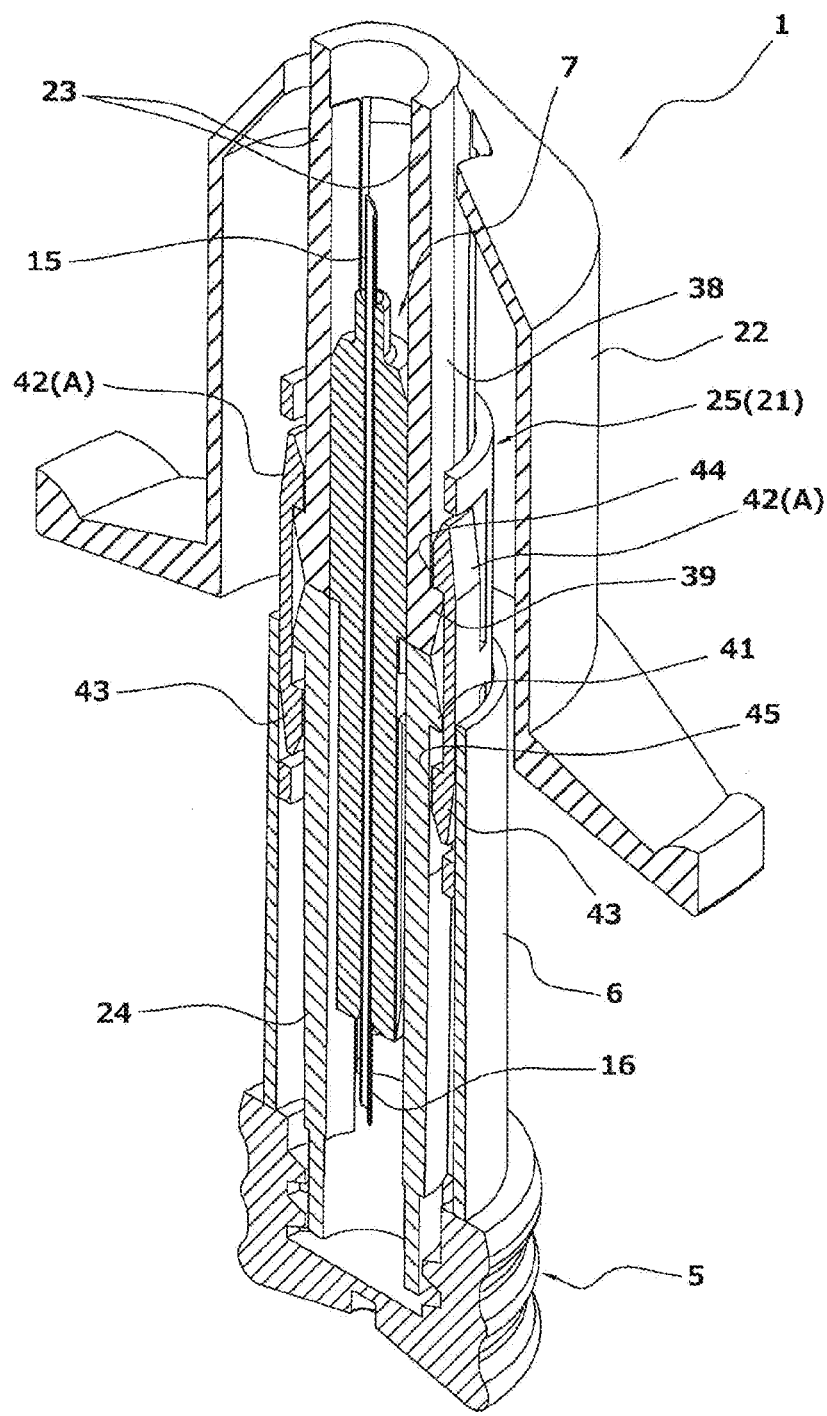
FIG. 30 is a perspective view in vertical section of an operation mechanism of a prefilled syringe according to a fourth embodiment of the present invention.

FIG. 30 illustrates only an operation mechanism of a prefilled syringe 1 of a before-use dissolving type according to a fourth embodiment of the present invention. The fourth embodiment has substantially the same construction as the second embodiment, except that the first connection rods 23 are molded integrally with the operation cylinder 22, and no spring is provided. Therefore, like components are designated by like reference characters, and will not be described in detail.

The present invention is not limited to the embodiments described above but, as required, modifications may be made to the embodiments. For example, the second gasket is not necessarily required to be inserted in the outer cylinder in vacuum, but the second containing space may be filled with air. In this case, there is a possibility that the second gasket is raised from the first gasket after the mixing. To cope with this, the gas should be removed before the administration. Further, the hollow needle may be molded integrally with the outer cylinder without the provision of the base plate. In this case, the hollow needle may have a communication opening provided in a side portion thereof adjacent to the rear end thereof for communication with the inner hole, so that a rear end portion of the hollow needle can be open in the first containing space through the communication opening.

REFERENCE SIGNS LIST

1 PREFILLED SYRINGE
2 OUTER CYLINDER
3 HOLLOW NEEDLE
4 FIRST GASKET
5 SECOND GASKET
6 PLUNGER
7 INJECTION NEEDLE (DOUBLE HEAD NEEDLE)
12 FIRST ENGAGEMENT PORTION
13 SECOND ENGAGEMENT PORTION
50 INJECTION NEEDLE ATTACHMENT
51 ATTACHMENT PORT
52 CAP

The invention claimed is:

1. A prefilled and before-use mixing syringe comprising:
an outer cylinder having a front end forward of a rear end;
an axially extending hollow needle in the outer cylinder, said hollow needle having
a front end and rear end, said needle front end being closer to said outer cylinder front end than said needle rear end, and
a cutting edge at its front end;
a first gasket provided in the outer cylinder forward of the front end of the hollow needle, said first gasket extending forwardly from a rear side to a front side; and
a second gasket provided in the outer cylinder forward of the first gasket, said second gasket extending forwardly from a rear side to a front side;
wherein a first space containing a liquid is defined in the outer cylinder rearwardly of the first gasket rear side, and communicates with the rear end of the hollow needle, the syringe further comprising:
non-rotatively and complementarily shaped first and second engagement portions respectively provided at the front side of the first gasket and the rear side of the second gasket,
said first engagement portion being at the front side of the first gasket and having a forwardly facing front face,
said second engagement portion being at the rear side of the first gasket and having a rearwardly facing rear face;
wherein
a second space containing a drug to be mixed with the liquid is defined between the first gasket and the second gasket in the outer cylinder with the front face of the first engagement portion and the rear face of the second engagement portion abutting against each other to keep the first and second engagement portions out of engagement with each other,
the hollow needle is moved axially relatively toward the first gasket to penetrate through the first gasket to cause the first containing space and the second containing space to communicate with each other through the hollow needle, and
the first gasket and the second gasket are rotated relative to each other to disengage said first engagement portion front face from said second engagement portion rear face whereby the first and second gaskets may be moved axially toward each other to reduce a volume of the second containing space.

2. The prefilled and before-use mixing syringe according to claim 1, further comprising a plunger to be operated for pushing the second gasket rearward, wherein
the first gasket is axially movable in the outer cylinder,
the second gasket is axially movable and rotatable in the outer cylinder, whereby the second gasket
when initially pushed rearward moves the first gasket rearward, whereby the hollow needle penetrates through the first gasket to cause the first containing space and the second containing space to communicate with each other through the hollow needle,
when further pushed rearward further moves the first gasket rearward to reduce a volume of the first containing space with the hollow needle defining a communication passage through which the liquid is transferred from the first containing space into the second containing space, and
when rotated relative to the first gasket and moved axially toward the first gasket, the volume of the second containing space is reduced.

3. The prefilled and before-use mixing syringe according to claim 1,
wherein the second gasket is inserted into the outer cylinder in vacuum, whereby the second containing space is kept in vacuum.

4. The prefilled and before-use mixing syringe according to claim 1,
wherein a gas which permits the first gasket and the hollow needle to move relatively toward each other to pierce the first gasket with the hollow needle is contained together with the liquid in the first containing space.

5. The prefilled and before-use mixing syringe according to claim 1, further comprising a double head needle provided on a front side of the second gasket,
wherein the double head needle when moved axially rearward toward the second gasket penetrates through the second gasket, thereby functioning as an outlet passage through which the liquid mixture drug containing the liquid and the drug flows out from the second containing space.

6. The prefilled and before-use mixing syringe according to claim 1,
wherein the outer cylinder has an attachment port provided at the rear end thereof for receiving an injection needle attachment,
the syringe further comprising a cap removably attached to the attachment port to seal the attachment port,
wherein the rear end of the hollow needle communicates with the attachment port.

7. A prefilled and before-use mixing syringe comprising:
an outer cylinder having a rear end;
a hollow needle extending axially in the outer cylinder from the outer cylinder rear end;
a first gasket in the outer cylinder spaced in a first axial direction from the hollow needle, wherein a first space containing liquid is defined in the outer cylinder between said first gasket and said outer cylinder rear end, said first containing space communicating with the hollow needle at said outer cylinder rear end;
a second gasket in the outer cylinder spaced in the first axial direction from the first gasket, wherein a second space containing a drug to be mixed with the liquid is defined between the first gasket and the second gasket in the outer cylinder a first engagement portion facing in said first axial direction from said first gasket;

a second engagement portion on said second gasket facing said first engagement portion, wherein in one rotational position of said second engagement portion within said outer cylinder, said first and second engagement portions engage to provide said second containing space, and in a second rotational position of said second engagement portion within said outer cylinder, said first and second engagement portions when axially engaged provide a reduced volume of said second containing space;

wherein the hollow needle when moved axially toward the first gasket penetrates through the first gasket to cause the first containing space and the second containing space to communicate with each other through the hollow needle.

8. The prefilled and before-use mixing syringe according to claim 7, wherein:

said first and second engagement portions are each tapered from a base to a facing surface axially spaced from the base, said first engagement portion facing surface engages said second engagement portion facing surface in said first rotational position, and said first and second engagement portions axially overlap each other in said second rotational position with said facing surfaces engaging said bases.

9. The prefilled and before-use mixing syringe according to claim 8, further comprising a plunger to be operated for pushing the second gasket rearward, wherein:

the first gasket is axially movable in the outer cylinder;

the second gasket is axially movable and rotatable in the outer cylinder; and when the second gasket is pushed toward said outer cylinder rear end, said engaging facing surfaces of said engagement portions push the first gasket rearward, whereby the hollow needle penetrates through the first gasket to cause the first containing space and the second containing space to communicate with each other through the hollow needle, when the second gasket is further pushed toward said outer cylinder rear end, said first gasket is moved toward said outer cylinder rear end to reduce a volume of the first containing space with the hollow needle providing a communication passage through which the liquid is transferred from the first containing space into the second containing space, and when the second gasket, is rotated relative to the first gasket and moved axially toward the first gasket, the engagement portion facing surfaces are rotationally spaced from one another whereby axial movement of the second gasket toward the first gasket causes said first and second engagement portions to axially overlap to reduce the volume of the second containing space.

10. The prefilled and before-use mixing syringe according to claim 7, wherein the second gasket is inserted into the outer cylinder in vacuum, whereby the second containing space is kept in vacuum.

11. The prefilled and before-use mixing syringe according to claim 7, wherein a gas which permits the first gasket and the hollow needle to move relatively toward each other to pierce the first gasket with the hollow needle is contained together with the liquid in the first containing space.

12. The prefilled and before-use mixing syringe according to claim 1, further comprising a double head needle spaced from said second gasket in said first axial direction, said double head needle being axially movable toward the second gasket to penetrate through the second gasket to define an outlet passage through which the liquid mixture drug containing the liquid and the drug may flow out from the second containing space.

13. The prefilled and before-use mixing syringe according to claim 1, further comprising:

an attachment port at the outer cylinder rear end for receiving an injection needle attachment; and a cap removably attached to the attachment port to seal the attachment port;

wherein the hollow needle communicates with the attachment port.

* * * * *